(12) United States Patent
Wang et al.

(10) Patent No.: US 12,714,829 B2
(45) Date of Patent: Aug. 25, 2026

(54) GROWABLE CONTINUUM INSTRUMENT AND SURGICAL ROBOT

(71) Applicants: The First Affiliated Hospital of Naval Medical University, Shanghai (CN); BEIJING SURGERII ROBOTICS COMPANY LIMITED, Beijing (CN)

(72) Inventors: Linhui Wang, Shanghai (CN); Bo Yang, Shanghai (CN); Chao Zhang, Shanghai (CN); Zongqin Zhang, Shanghai (CN); Tie Zhou, Shanghai (CN); Hong Xu, Shanghai (CN); Chengwu Xiao, Shanghai (CN); Xiaofeng Wu, Shanghai (CN); Kai Xu, Shanghai (CN)

(73) Assignees: THE FIRST AFFILIATED HOSPITAL OF NAVAL MEDICAL UNIVERSITY, Shanghai (CN); BEIJING SURGERII ROBOTICS COMPANY LIMITED, Beijing (CN)

( * ) Notice: Subject to any disclaimer, the term of this patent is extended or adjusted under 35 U.S.C. 154(b) by 611 days.

(21) Appl. No.: 18/080,866

(22) Filed: Dec. 14, 2022

(65) Prior Publication Data

US 2023/0181873 A1 Jun. 15, 2023

(30) Foreign Application Priority Data

Dec. 15, 2021 (CN) ......................... 202111530243.2

(51) Int. Cl.
*A61M 25/01* (2006.01)
*A61B 34/30* (2016.01)

(52) U.S. Cl.
CPC ......... *A61M 25/0138* (2013.01); *A61B 34/30* (2016.02); *A61M 25/0155* (2013.01); *A61B 2034/301* (2016.02)

(58) Field of Classification Search
CPC .......... A61M 25/0138; A61M 25/0155; A61M 25/0023; A61M 25/0043; A61M 25/0147;
(Continued)

(56) References Cited

U.S. PATENT DOCUMENTS

2005/0273085 A1* 12/2005 Hinman ............... A61B 1/0055 606/1
2007/0135803 A1* 6/2007 Belson ............... A61B 1/00154 606/1

(Continued)

FOREIGN PATENT DOCUMENTS

CN 106361386 A 2/2017
CN 206443718 U 8/2017

(Continued)

OTHER PUBLICATIONS

Extended European Search Report in related European Application No. 22213660.8 dated May 19, 2023 (10 pages).

(Continued)

*Primary Examiner* — John R Downey
*Assistant Examiner* — Karmel J Webster
(74) *Attorney, Agent, or Firm* — Bayes PLLC

(57) ABSTRACT

A growable continuum instrument includes a growable tube and one or more serially connected continuum structures. The growable tube includes an inner layer, an outer layer, and a fluid chamber between the inner and outer layers. The growable tube includes a turnable region where the inner and outer layers are connected and turnable. The continuum structure is located in the growable tube. The continuum structure includes a plurality of spacer discs and a plurality of connecting structures. The connecting structure includes one or more flexible structural bones, the two ends of which are respectively fixedly connected with the adjacent spacer discs, and are distributed along the circumferential direction (Continued)

of the spacer discs. The plurality of connecting structures include at least a first and second connecting structures, and the flexible structural bones of the first and second connecting structures are distributed differently along the circumferential direction of the spacer disc.

16 Claims, 26 Drawing Sheets

(58) Field of Classification Search
CPC .. A61M 2025/0024; A61M 2025/0161; A61M 25/005; A61M 25/0113; A61M 25/0116; A61M 25/0119; A61M 25/0122; A61M 25/0144; A61M 2025/0175; A61B 34/30; A61B 2034/301; A61B 2017/00314; A61B 2017/00323; A61B 2017/00336; A61B 34/70
See application file for complete search history.

(56) References Cited

U.S. PATENT DOCUMENTS

| | | | | |
|---|---|---|---|---|
| 2019/0192129 | A1 | 6/2019 | Xu et al. | |
| 2019/0193260 | A1* | 6/2019 | Xu | A61B 34/30 |
| 2020/0113557 | A1* | 4/2020 | Sholev | A61M 25/0147 |
| 2020/0142013 | A1* | 5/2020 | Wong | G01R 33/34023 |

FOREIGN PATENT DOCUMENTS

| | | | |
|---|---|---|---|
| CN | 113079287 | A | 7/2021 |
| CN | 114699621 | A | 7/2022 |
| CN | 217960929 | U | 12/2022 |
| CN | 217960930 | U | 12/2022 |
| EP | 3903711 | A1 | 11/2021 |

OTHER PUBLICATIONS

Search Report in related Chinese Application No. 2021115302432 dated Nov. 6, 2024 (3 pages).

* cited by examiner

GROWABLE CONTINUUM INSTRUMENT AND SURGICAL ROBOT

CROSS-REFERENCE TO RELATED APPLICATION

The present application claims the benefits of priority to Chinese Application No. 202111530243.2, filed Dec. 15, 2021, the entire contents of which are expressly incorporated herein by reference.

TECHNICAL FIELD

The present application relates to the field of continuum instrument, and in particular relates to growable continuum instrument and surgical robot.

BACKGROUND

Traditional disease diagnosis and surgical treatment are mainly divided into open diagnosis and surgery and intracavitary interventional diagnosis and treatment. Intracavitary interventional diagnosis or treatment is to make an incision on blood vessels and skin to form a channel without performing surgical operation to expose the lesion, or to reach the target position through the original cavity of the human body under the guidance of imaging device, so as to diagnose or treat the lesion locally, with the characteristics of less trauma.

Traditional intracavitary interventional surgery mainly relies on doctors to perform manual operations. In order to reduce the burden on doctors and improve the efficiency and safety of intracavitary intervention, the method of using intracavitary interventional instrument to assist interventional diagnosis or surgery has gradually become a research hotspot in the industry. The intracavitary interventional instruments can be controlled remotely to eliminate the danger resulting from physiological trembling and fatigue mis-operation of doctor during manual operation.

However, for the sake of operation control, the currently used intracavity interventional instruments usually make the interventional instruments have isotropic bending. As a result, the flexibility of the interventional instruments is relatively poor, the bending space is limited, and it cannot adapt to the complex curved human cavity, making it easy to cause damage to the cavity.

SUMMARY

In one aspect, a growable continuum instrument is provided. The growable continuum instrument includes a growable tube including an inner layer, an outer layer, and a fluid cavity between the inner layer and the outer layer. The fluid cavity is used to accommodate fluids. The growable tube includes a turnable area at its distal end, and the inner layer and the outer layer are connected and turnable in the turnable area. The growable continuum instrument also includes one or more serially connected continuum structures disposed in a channel surrounded by the inner layer of the growable tube. The continuum structure is bendable to drive the growable tube to bend. The continuum structure includes a plurality of spacer discs and a plurality of connecting structures. The connecting structure includes one or more flexible structural bones. A first end and a second end of the one or more flexible structural bones are respectively fixedly connected to the adjacent spacer discs. The one or more flexible structural bones are distributed along the circumferential direction of the spacer disc. The plurality of connecting structures includes at least a first connecting structure and a second connecting structure. The first connecting structure includes one or more first flexible structural bones. The second connecting structure includes one or more second flexible structural bones. A distribution of the one or more first flexible structural bones along the circumferential direction of the spacer disc is different from a distribution of the one or more second flexible structural bones along the circumferential direction of the spacer disc.

In other aspects, the present application also provides a surgical robot, including the growable continuum instrument described in any of the embodiments disclosed in the present application.

BRIEF DESCRIPTION OF THE DRAWINGS

In order to explain the technical solutions in the embodiments of the present disclosure more clearly, the accompanying drawings used in the description of the embodiments of the present disclosure will be briefly introduced below. The accompanying drawings in the following description only show some of the embodiments of the present disclosure, and for those of ordinary skill in the art, other embodiments would also have been obtained from the contents of the embodiments of the present disclosure and these accompanying drawings without involving any inventive effort.

FIG. 2(*b*) shows a three-dimensional structure schematic diagram of a continuum structure according to other embodiments of the present disclosure;

FIG. 2(*c*) shows a three-dimensional structure schematic diagram of a continuum structure according to other embodiments of the present disclosure;

FIG. 4(*b*) shows a schematic diagram of projection of the flexible structural bones of the continuum structure along an axial direction according to other embodiments of the present disclosure;

FIG. 5(*b*) shows a three-dimensional structure schematic diagram of a continuum structure according to other embodiments of the present disclosure;

FIG. 5(*c*) shows a three-dimensional structure schematic diagram of a continuum structure according to other embodiments of the present disclosure;

FIG. 5(*d*) shows a three-dimensional structure schematic diagram of a continuum structure according to other embodiments of the present disclosure;

FIG. 5(*e*) shows a three-dimensional structure schematic diagram of a continuum structure according to other embodiments of the present disclosure;

FIG. 5(*f*) shows a three-dimensional structure schematic diagram of a continuum structure according to other embodiments of the present disclosure;

FIG. 6(*b*) shows a schematic diagram of projection of the flexible structural bones of the continuum structure along an axial direction according to other embodiments of the present disclosure;

FIG. 6(*c*) shows a schematic diagram of projection of the flexible structural bones of the continuum structure along an axial direction according to other embodiments of the present disclosure;

FIG. 6(*d*) shows a schematic diagram of projection of the flexible structural bones of the continuum structure along an axial direction according to other embodiments of the present disclosure;

FIG. 7(*b*) shows a schematic diagram of projection of the flexible structural bones of the continuum structure along an axial direction according to other embodiments of the present disclosure;

FIG. 7(*c*) shows a schematic diagram of projection of the flexible structural bones of the continuum structure along an axial direction according to other embodiments of the present disclosure;

FIG. 8(*b*) shows a schematic diagram of projection of the flexible structural bones of the continuum structure along an axial direction according to other embodiments of the present disclosure;

FIG. 9(*b*) shows a schematic diagram of projection of the flexible structural bones of the continuum structure along an axial direction according to other embodiments of the present disclosure;

FIG. 9(*c*) shows a schematic diagram of projection of the flexible structural bones of the continuum structure along an axial direction according to other embodiments of the present disclosure;

FIG. 15(*b*) shows a schematic diagram of projection of driving structural bones of the continuum instrument along an axial direction according to other embodiments of the present disclosure;

FIG. 15(*c*) shows a schematic diagram of projection of driving structural bones of the continuum instrument along an axial direction according to other embodiments of the present disclosure;

FIG. 18(*b*) shows a structural schematic diagram of a distal portion of the growable tube according to some embodiments of the present disclosure;

FIG. 19(*b*) shows a structural schematic diagram of a part of driving mechanism according to other embodiments of the present disclosure;

DETAILED DESCRIPTION

To make the solved technical problems, used technical solutions, and achieved technical effects of the present disclosure more clearly, the technical solutions of the embodiments of the present disclosure will be further described in detail below with reference to the accompanying drawings. Obviously, the described embodiments are only exemplary embodiments, but not all of embodiments, of the present disclosure.

In the description of the present disclosure, it should be noted that, orientational or positional relationships indicated by the terms "center", "upper", "lower", "left", "right", "vertical", "horizontal", "inner", "outer" and the like are the orientational or positional relationships shown based on the accompanying drawings, and are only for ease of describing the present disclosure and simplifying the description, rather than indicating or implying that the apparatus or element referred to must have a specific orientation or be constructed and operated in a specific orientation, and therefore cannot be construed as limiting the present disclosure. In addition, the terms "first" and "second" are used for descriptive purposes only, and cannot be understood as indicating or implying relative importance. In the description of the present disclosure, it should be noted that, unless otherwise specified and defined, the term "mount", "connected", and "connect", or "couple" should be comprehended in a broad sense. For example, the term may be a fixed connection or a detachable connection; or may be a mechanical connection or an electrical connection; may be a direct connection or an indirect connection via an intermediate medium; or may be internal communication between two elements. For those of ordinary skill in the art, specific meanings of the foregoing terms in the present disclosure may be understood based on specific situations. In the present disclosure, an end close to an operator (e.g., a surgeon) is defined as a proximal end, a proximal portion, a rear end, or a rear portion, and an end close to an object to be operated (e.g., a patient) is defined as a distal end, a distal portion, a front end, or a front portion. It may be understood by those skilled in the art that the embodiments of the present disclosure may be used for a medical instrument or a surgical robot, and may also be used for other non-medical apparatus.

Figure 1:
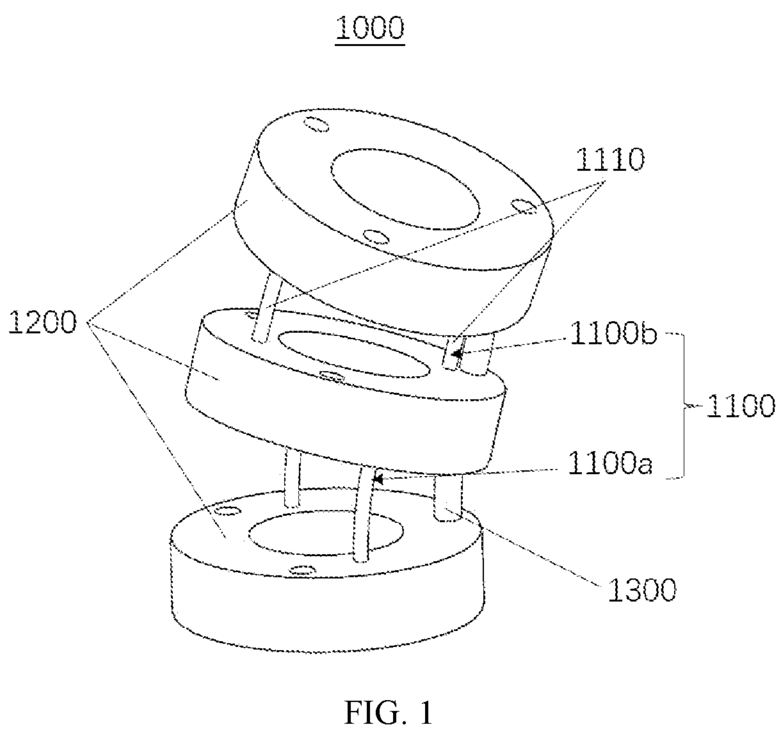
FIG. 1 shows a three-dimensional structure schematic diagram of a continuum structure according to some embodiments of the present disclosure.

FIG. 1 shows a three-dimensional structure schematic diagram of a continuum structure 1000 according to some embodiments of the present disclosure. In some embodiments, as shown in FIG. 1, the serially connected continuum structure 1000 may include a plurality of spacer discs 1200 and a plurality of connecting structures 1100. The connecting structure 1100 may include one or more flexible structural bones 1110, the first end and the second end of the one or more flexible structural bones 1110 are respectively fixedly connected with the adjacent spacer discs 1200, and one or more flexible structural bones 1110 are distributed along the circumference of the spacer disc 1200. Wherein, the plurality of connecting structures 1100 may at least include connecting structure 1100*a* and connecting structure 1100*b*. Those skilled in the art can understand that although FIG. 1 only shows two types of connecting structures 1100*a*, 1100*b*, while the plurality of connecting structures 1100 may also include other types of connecting structure.

Figure 2A:
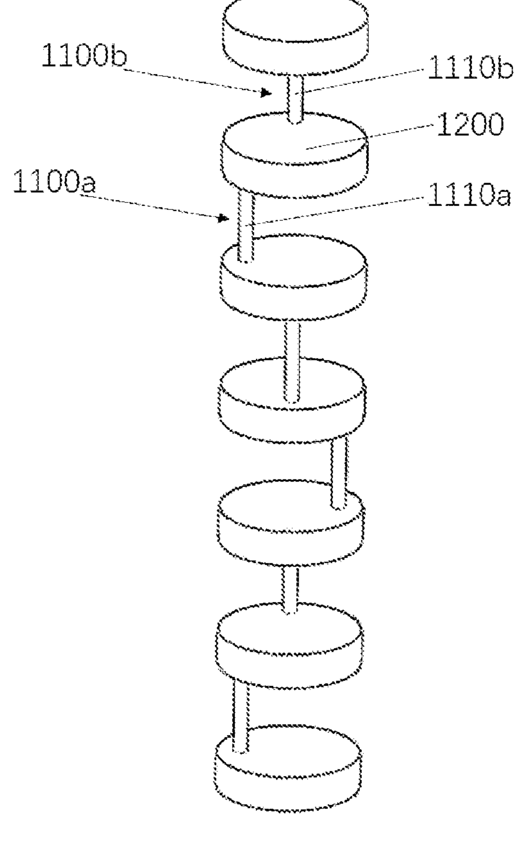
FIG. 2(*a*) shows a three-dimensional structure schematic diagram of a continuum structure according to other embodiments of the present disclosure.
Figure 2B:
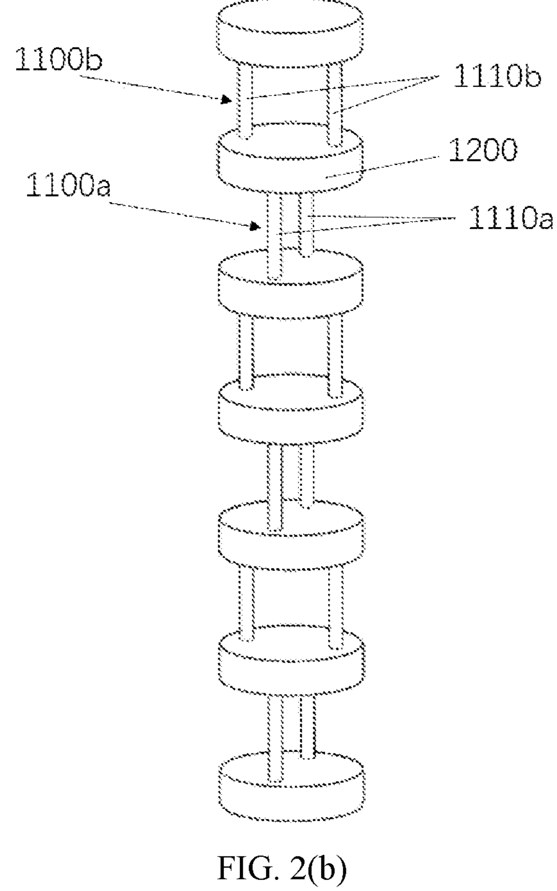
Figure 2C:
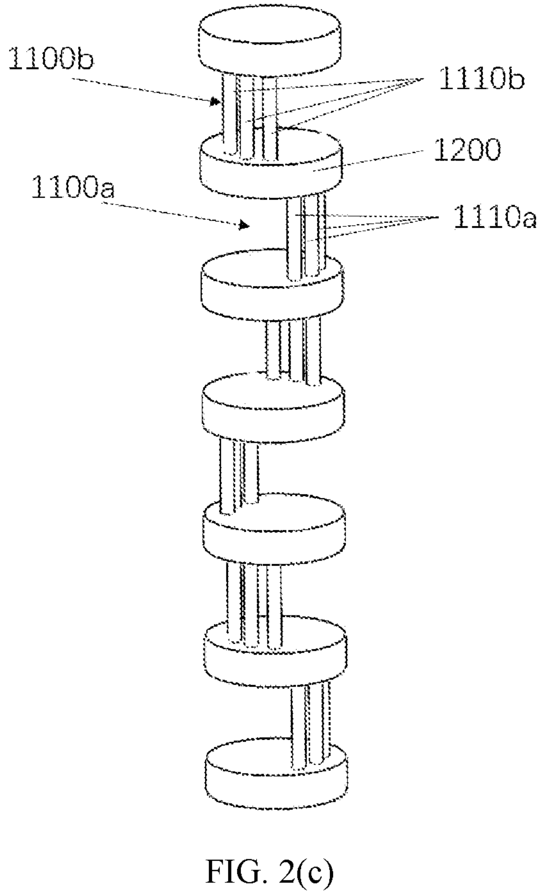

FIGS. 2(*a*)-2(*c*) shows schematic diagrams of different three-dimensional structures of the continuum structure 1000 according to some embodiments of the present disclosure. As shown in FIGS. 2(*a*)-2(*c*), the connecting structure 1100*a* may include one or more flexible structural bones 1110*a*, the connecting structure 1100*b* may include one or more flexible structural bones 1110*b*, and the circumferential distribution of one or more flexible structural bones 1110*a* along the spacer disc 1200 is different from the circumferential distribution of one or more flexible structural bones 1110*b* along the spacer disc 1200. As shown in FIG. 2(*a*), the connecting structure 1100*a* may include one flexible structural bone 1110*a*, and the connecting structure 1100*b* may include one flexible structural bone 1110*b*. As shown in FIG. 2(*b*), the connecting structure 1100*a* may include two flexible structural bones 1110*a*, and the connecting structure 1100*b* may include two flexible structural bones 1110*b*. As shown in FIG. 2(*c*), the connecting structure 1100*a* may include three flexible structural bones 1110*a*, and the connecting structure 1100*b* may include there flexible structural bones 1110*b*. It should be understood that the connecting structure 1100*a* may also include more flexible structural bones 1110*a*, and the connecting structure 1100*b* may also include more flexible structural bones 1110*b*.

Figure 3:
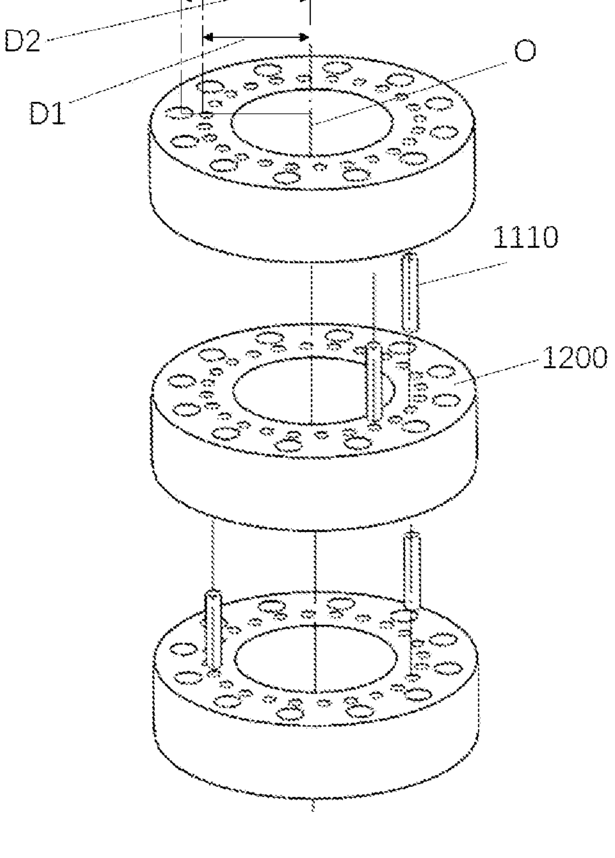
FIG. 3 shows a partially exploded schematic diagram of a continuum structure according to some embodiments of the present disclosure.

FIG. 3 shows a partially exploded schematic diagram of a continuum structure 1000 according to some embodiments of the present disclosure. It should be understood that a plurality of spacer discs 1200 may be arranged at intervals, and one or more flexible structural bones 1110 arranged in parallel along a central axis O of the continuum structure may be included between adjacent spacer discs 1200, as shown in FIG. 3. In some embodiments, one or more flexible structural bones 1110 may be distributed along the inner contour lines or inner circumference lines of the spacer disc 1200. It should be understood that the inner contour lines or inner circumference lines may include curves, arcs or straight lines distributed along the circumferential or radial direction from the central axis O of the continuum structure to the radial end surface of the spacer disc 1200. For example, one or more flexible structural bones 1110*a* or one or more flexible structural bones 1110*b* may be distributed in a circle, a curve, a rectangle, etc. along the inner contour lines or inner circumference lines of the spacer disc 1200.

Figure 4A:
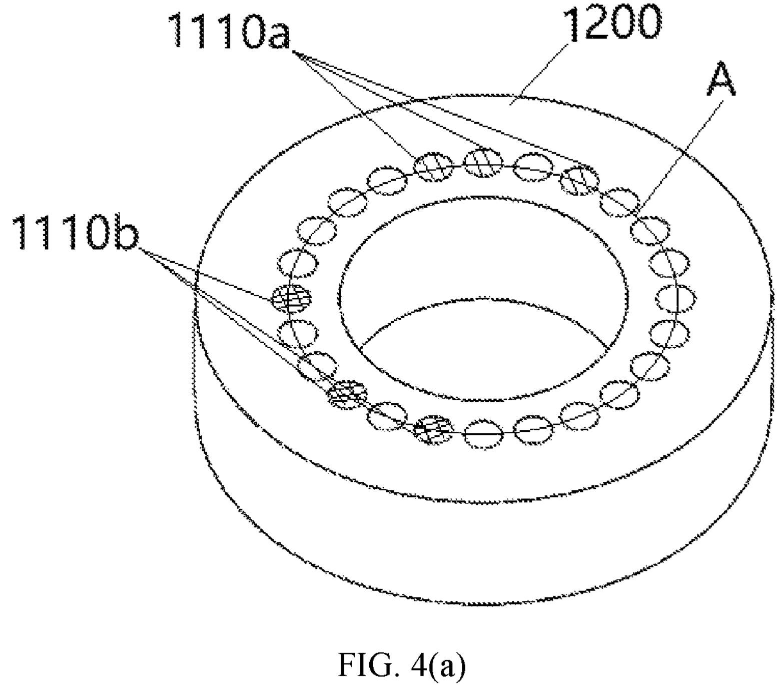
FIG. 4(*a*) shows a schematic diagram of projection of the flexible structural bones of the continuum structure along an axial direction according to some embodiments of the present disclosure.
Figure 4B:
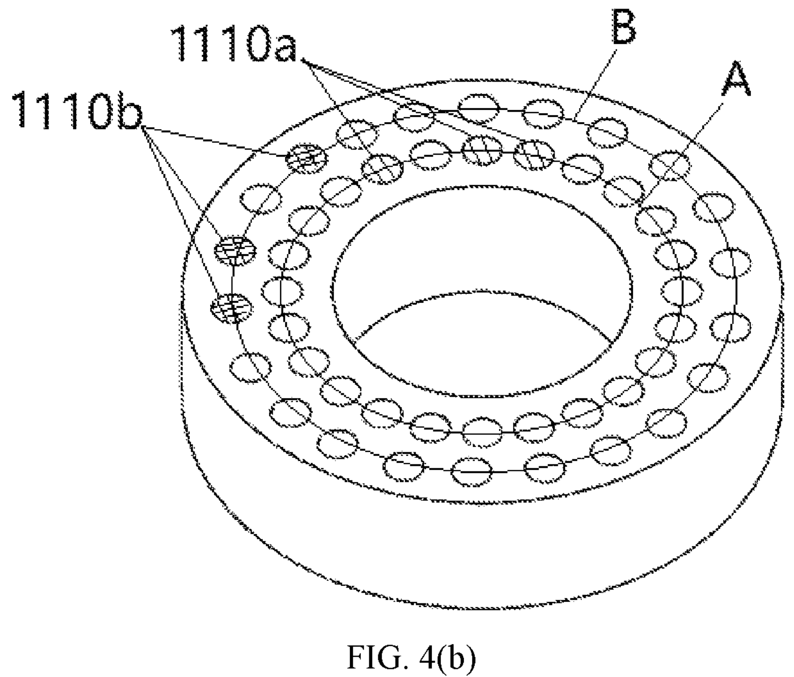
Figure 5A:
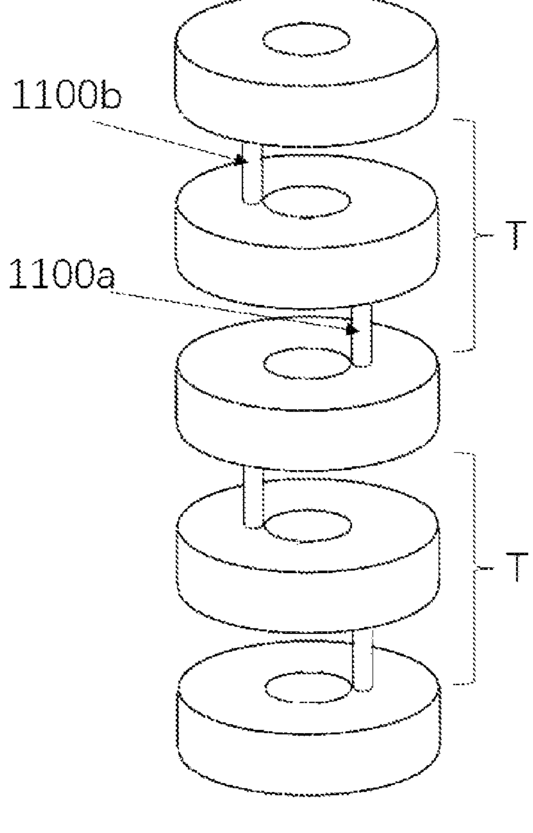
FIG. 5(*a*) shows a three-dimensional structure schematic diagram of a continuum structure according to other embodiments of the present disclosure.
Figure 5B:
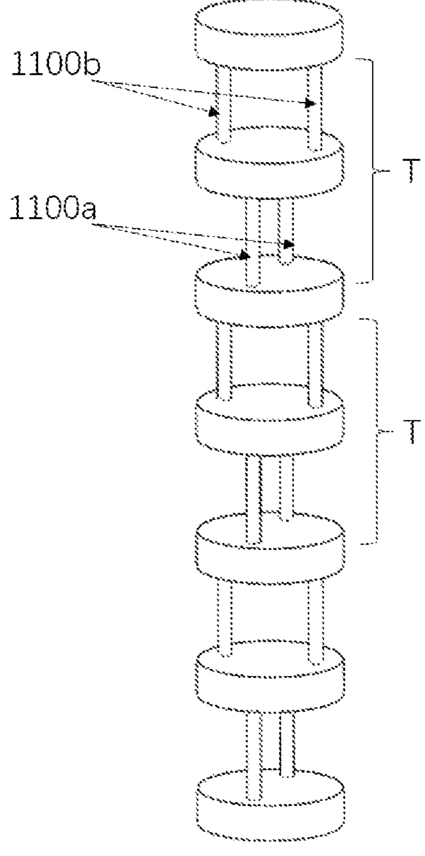
Figure 5C:
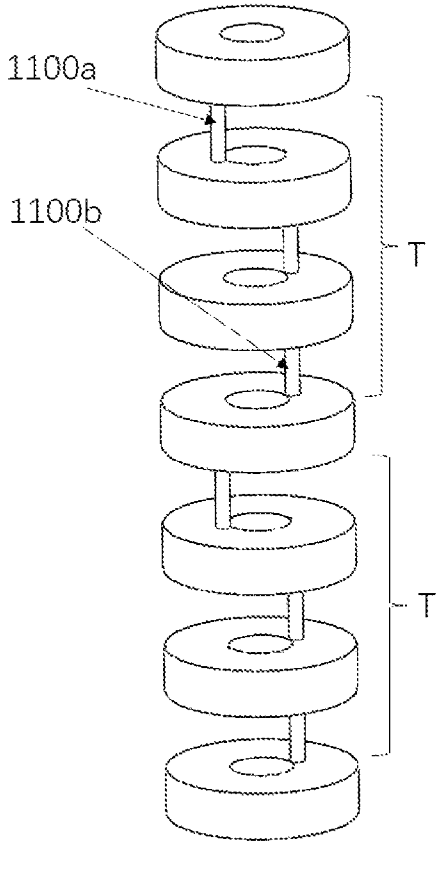
Figure 5D:
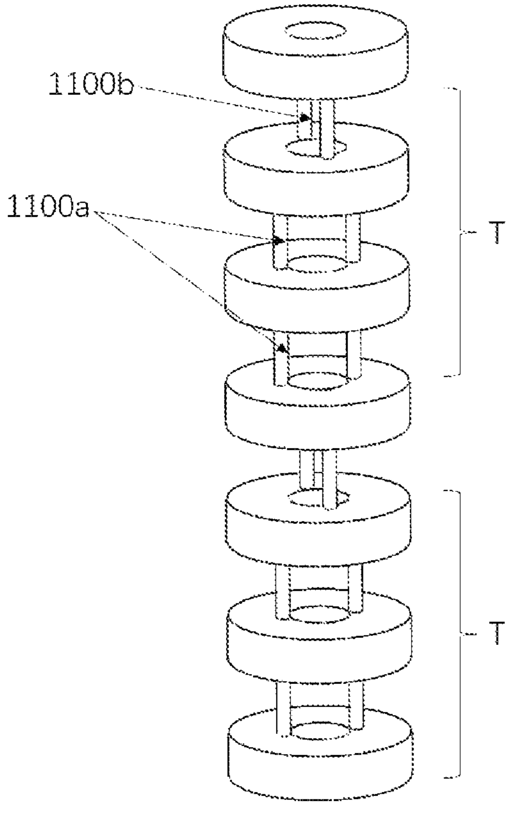
Figure 5E:
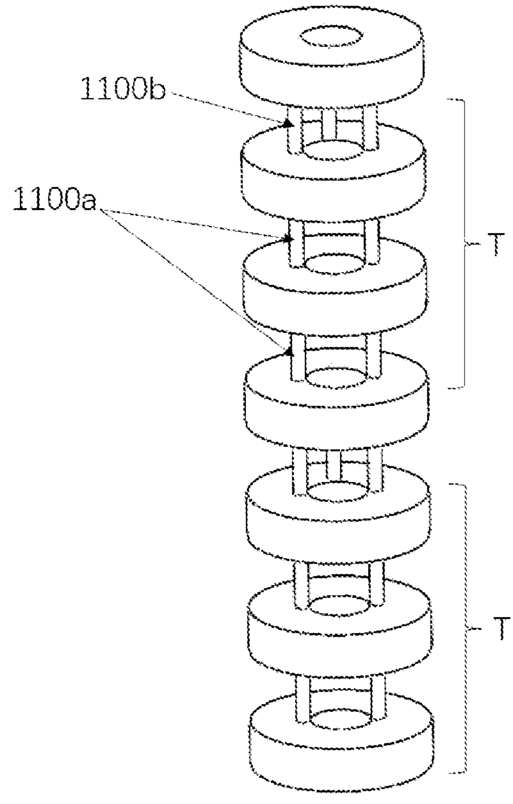
Figure 5F:
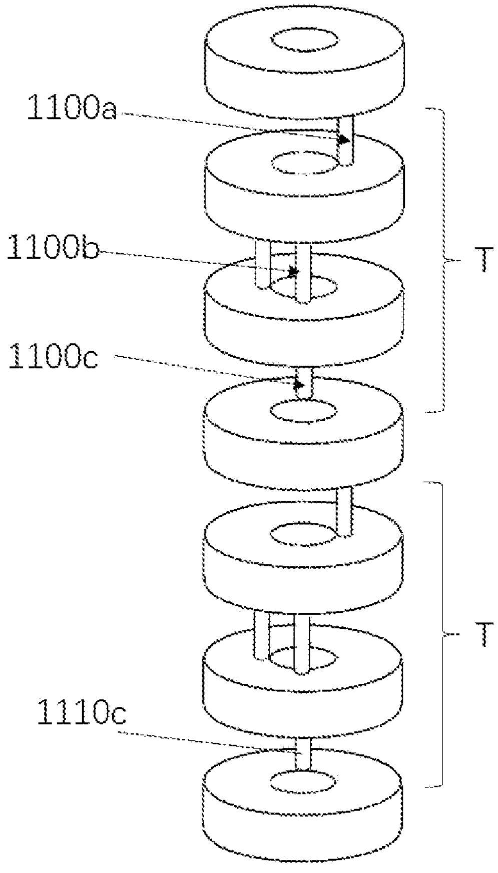
Figure 6A:
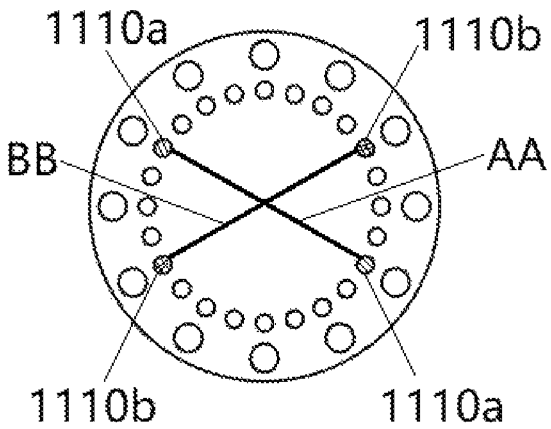
FIG. 6(*a*) shows a schematic diagram of projection of the flexible structural bones of the continuum structure along an axial direction according to other embodiments of the present disclosure.
Figure 6B:
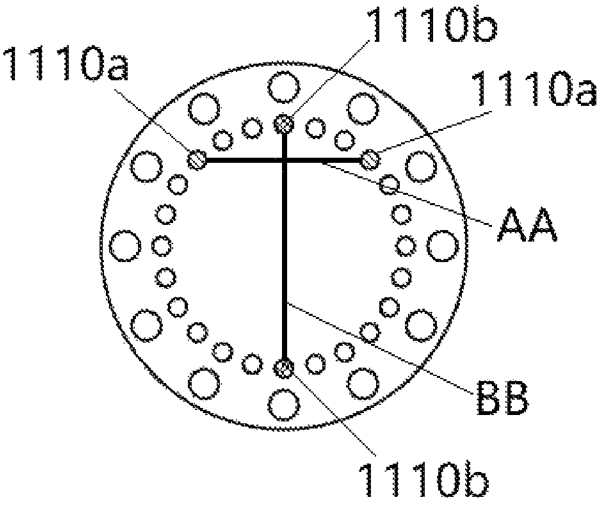
Figure 6C:
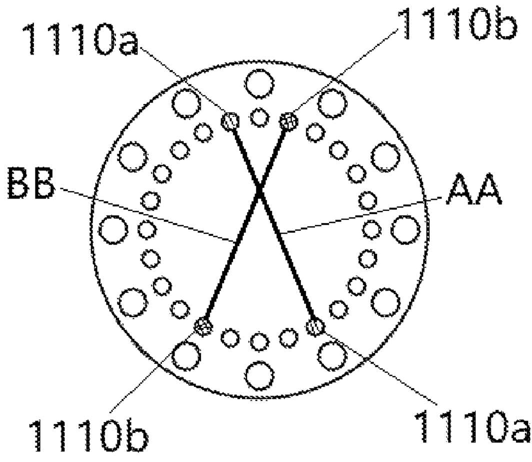
Figure 6D:
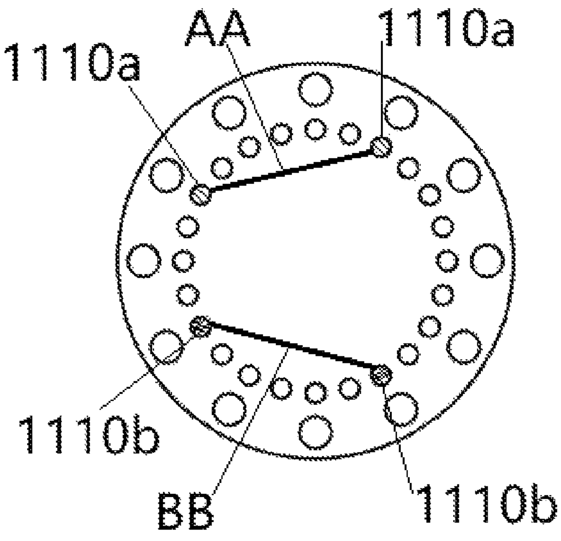

FIG. 4(*a*) and FIG. 4(*b*) respectively show schematic diagrams of different projections of the flexible structural bones of the continuum structure along the axial direction according to some embodiments of the present disclosure. In some embodiments, as shown in FIG. 4(*a*), the projections of one or more flexible structural bones 1110*a* and one or more flexible structural bones 1110*b* along the axial direction of the continuum structure can be distributed along the circumferential direction of the spacer disc 1200 and along the same circle A. Alternatively, as shown in FIG. 4(*b*), one or more flexible structural bones 1110*a* are respectively distributed along the circumferential direction of the spacer disc 1200 and along the circle A, and one or more flexible structural bones 1110*b* are respectively distributed along the circumferential direction of the spacer disc 1200 and along the circle B. The circle A is radially spaced apart from the circle B.

Those skilled in the art should understand that, one or more flexible structural bones 1110*a* or one or more flexible structural bones 1110*b* are distributed differently along the circumferential direction of the spacer disc 1200, including but not limited to, one or more flexible structural bones 1110*a* are distributed in a first area of the spacer disc 1200, and one or more flexible structural bones 1110*b* are distributed in a second area of the spacer disc 1200 different from the first area; alternatively, one or more flexible structural bones 1110*a* are distributed in a first area of the spacer disc 1200, and one or more flexible structural bones 1110*b* are distributed in a second area of the spacer disc 1200 partially overlapping the first area; alternatively, one or more flexible structural bones 1110*a* are distributed in a first area of the spacer disc 1200, one or more flexible structural bones 1110*b* are distributed a second area of the spacer disc 1200, and the first area and the second area are staggered by a certain included angle along the circumference of the spacer disc; alternatively, the numbers of the flexible structural bones 1110*a* and the flexible structural bones 1110*b* are different, resulting in different distributions thereof; alternatively, the number of flexible structural bones 1110*a* and the flexible structural bones 1110*b* are the same, but due to the difference in the distribution distance between the flexible structural bones, their distributions are different. The flexible structural bone 1110*a* and the flexible structural bone 1110*b* are distributed differently along the circumferential direction of the spacer disc 1200, so that the continuum structure can be bent in different directions, and the direction and degree of bending can be adjusted according to the number and distribution of the flexible structural bone, for example, the continuum structure can be bended toward a side where the flexible structural bones are less or no flexible structural bone is distributed.

FIGS. 5(*a*)-5(*f*) respectively show schematic diagrams of different three-dimensional structures of the continuum structure according to some embodiments of the present disclosure. In some embodiments, as shown in FIG. 5(*a*)-FIG. 5(*f*), the plurality of connecting structures 1100 may include one or more serially connected connecting structures 1100*a* and one or more serially connected connecting structures 1100*b*, and one or more serially connected connecting structures 1100*a* and one or more serially connected connecting structures 1100*b* are distributed periodically or non-periodically along the axial direction of the continuum structure. For example, one connecting structure 1100*a* and one connecting structure 1100*b* may be distributed alternately in order to form a plurality of periodic units T. As shown in FIG. 5(*a*), the connecting structure 1100*a* and the connecting structure 1100*b* respectively include one flexible structural bone, which are alternately connected in series along the axial direction of the continuum structure. As shown in FIG. 5(*b*), the connecting structure 1100*a* and the connecting structure 1100*b* respectively include two flexible structural bones, which are alternately connected in series along the axial direction of the continuum structure. As shown in FIG. 5(*c*), the connecting structure 1100*a* and the connecting structure 1100*b* respectively include one flexible structural bone, and one connecting structure 1100*a* and a plurality of serially connected connecting structures 1100*b* may be distributed alternately in sequence. It should be understood that one or more connecting structures 1100*a* and one or more serially connected connecting structures 1100*b* may also be distributed non-periodically, for example, as shown in FIG. 2(*c*).

As shown in FIG. 5(*d*), the connecting structure 1100*a* and the connecting structure 1100*b* respectively include two flexible structural bones, and a plurality of serially connected connecting structures 1100*a* and one connecting structure 1100*b* can be distributed alternately in sequence. As shown in FIG. 5(*e*), the connecting structure 1100*a* include two flexible structural bones, the connecting structure 1100*b* include three flexible structural bones, and a plurality of serially connected connecting structures 1100*a* and one connecting structure 1100*b* can be distributed alternately in sequence. It should be understood that a plurality of serially connected connecting structures 1100*a* and one connecting structure 1100*b* may also be distributed non-periodically. It should be understood that a plurality of serially connected connecting structures 1100*a* and a plurality of serially connected connecting structures 1100*b* may be alternately distributed in sequence, periodically or non-periodically, although not shown in the Figure. It should be understood that the number of flexible structural bones included in the connecting structure 1100*a* and the connecting structure 1100*b* in some embodiments of the present disclosure may include, but not limited to, one, two, three or more. The above embodiments are only examples, and the present disclosure is not limited thereto.

In some embodiments, as shown in FIG. 5(*f*), a plurality of connecting structures 1100 may further include one or more types of additional connecting structures 1100*c*. One or more serially connected additional connecting structures 1100*c*, one or more serially connected connecting structures 1100*a* and one or more serially connected connecting structures 1100*b* are distributed periodically or non-periodically along the axial direction of the continuum structure. It should be understood that the additional connecting structure 1100*c* may include one or more flexible structural bones 1110*c*, and a distribution of the one or more flexible structural bones 1110*c* along the circumference of the spacer disc 1200 is different from the circumferential distribution of the flexible structural bones 1110*a* and/or the flexible structural bones 1110*b*. FIG. 5(*f*) shows one flexible structural bone 1110*c* by way of example only. The number and distribution of flexible structural bone can vary for the various additional connecting structures. For example, as shown in FIG. 5(*f*), one additional connecting structure 1100*c*, one connecting structure 1100*a* and one connecting structure 1100*b* may be alternately distributed in sequence to form a plurality of periodic units T. It should be understood that one additional connecting structure 1100*c*, one connecting structure 1100*a* and a plurality of serially connected connecting structures 1100*b* may be distributed alternately in sequence or non-periodically. It should be understood that a plurality of additional connecting structures 1100*c*, a plurality of serially connected connecting structures 1100*a* and one connecting structure 1100*b* may be alternately distributed in sequence or non-periodically. It should be understood that one additional connecting structures 1100*c*, a plurality of serially connected connecting structures 1100*a* and a plurality of serially connected connecting structures 1100*b* may be alternately distributed in sequence or non-periodically. It should be understood that a plurality of serially connected additional connecting structures 1100*c*, a plurality of serially connected connecting structures 1100*a* and a plurality of serially connected connecting structures 1100*b* may be alternately distributed in sequence or non-periodically. It should be understood that multiple types of additional connecting structures 1100*c*, a plurality of serially connected connecting structures 1100*a* and a plurality of serially connected connecting structures 1100*b* may be alternately distributed in sequence or non-periodically. The above are only examples, and the present disclosure is not limited thereto.

It should be understood that the embodiments of the present disclosure may also include other periodic or aperiodic distribution or combined distribution, or distribute a plurality of connecting structures according to requirements to satisfy a specific bending direction. It should be understood that the number of flexible structural bones included in the one or more types of additional connecting structures 1100*c* in some embodiments of the present disclosure may include, but is not limited to, one, two, three or more. The above embodiments are only examples, and the present disclosure is not limited thereto. Various periodic or aperiodic distributions along the axial direction of the continuum structure can be achieved by one or more types of additional connecting structures 1100*c*, one or more serially connected connecting structures 1100*a* and one or more serially connected connecting structures 1100*b*, to increase the applicability of the continuum structure.

In some embodiments, the projections of the flexible structural bones 1110 (for example, the flexible structural bones 1110*a*, or 1110*b*, or 1110*c*) of a plurality of connecting structures 1100 along the axial direction of the continuum structure may be an asymmetrical distribution (for example, refer to FIG. 4(*a*) and FIG. 4(*b*)) or a non-centrosymmetric distribution. In the present disclosure, a symmetrical distribution may include an axisymmetric distribution and a centrosymmetric distribution. For example, a non-centrosymmetric distribution may include, but is not limited to, an axisymmetric distribution with the symcenter not passing through the center of the spacer disc.

It should be understood that projections of a plurality of flexible structural bones 1110*a* along the axial direction may be distributed asymmetrically or non-centrosymmetrically; alternatively, projections of a plurality of flexible structural bones 1110*b* along the axial direction may be distributed asymmetrically or non-centrosymmetrically; alternatively, projections of one or more flexible structural bones 1110*a* and one or more flexible structural bones 1110*b* along the axial direction may be distributed asymmetrically or non-centrosymmetrically. It should be understood that, it can also be that projections of flexible structural bones 1110*c* of one or more additional connecting structure 1100*c*, one or more flexible structural bones 1110*a* and one or more flexible structural bones 1110*b* along the axial direction is an asymmetrical distribution (for example, refer to FIG. 4(*a*) and FIG. 4(*b*)) or a non-centrosymmetric distribution.

In some embodiments, as shown in FIG. 2(*a*) and FIG. 5(*a*), the connecting structure 1100*a* may include one flexible structural bone 1110*a*, the connecting structure 1100*b* may include one flexible structural bone 1110*b*, and the flexible structural bone 1110*a* and the flexible structural bone 1110*b* are staggered by an included angle along the circumferential direction of the spacer disc 1200. For example, projections of the flexible structural bone 1110*a* and the flexible structural bone 1110*b* along the axial direction may be distributed along the same circle along the circumferential direction of the spacer disc 1200 and spaced apart from each other in the circumferential direction, as shown in FIG. 4(*a*). It should be understood that projections of the flexible structural bone 1110*a* and the flexible structural bone 1110*b* along the axial direction may be distributed along different circles along the circumferential direction of the spacer disc 1200 and spaced apart from each other in the circumferential direction or in the radial direction, as shown in FIG. 4(*b*). The included angle may include an included angle formed by the central axis O and the projections of the flexible structural bones 11110*a* and the flexible structural bones 1110*b*.

In some embodiments, as shown in FIG. 5(*b*), FIG. 5(*d*) and FIG. 5(*e*), the connecting structure 1100*a* may include a plurality of flexible structural bones 1110*a*, and the connecting structure 1100*b* may include a plurality of flexible structural bones 1110*b*. FIG. 6(*a*)-FIG. 6(*d*) show schematic diagrams of different projections of the flexible structural bones of the continuum structure along the axial direction according to some embodiments of the present disclosure. As shown in FIG. 6(*a*)-FIG. 6(*d*), a plurality of flexible structural bones 1110*a* form a connecting line AA, and a plurality of flexible structural bones 1110*b* form a connecting line BB. For example, the connecting line AA may be a straight line formed by two flexible structural bones 1110*a*, and the connecting line BB may be a straight line formed by two flexible structural bones 1110*b*, as shown in FIG. 6(*a*)-FIG. 6(*d*). It should be understood that the connecting line AA may also be a straight line formed by three or more flexible structural bones 1110*a*, and the connecting line BB may be a straight line formed by three or more flexible structural bones 1110*b*.

The projections of connecting line AA and connecting line BB along the axial direction may include at least one of the following distributions: connecting line AA and connecting line BB intersect at an angle at the central axis O of the continuum structure (refer to FIG. 6(*a*)), the connecting line BB passes through the central axis O of the continuum structure and intersects at an angle with the connecting line AA outside the central axis O of the continuum structure (refer to FIG. 6(*b*)), the connecting line AA and the connecting line BB deviate from the central axis O of the continuum structure and intersects (refer to FIG. 6(*c*)), or the connecting line AA and connecting line BB deviate from the central axis O of the continuum structure and intersect on their extended lines (refer to FIG. 6(*d*) shown). It should be understood that the connecting line AA and the connecting line BB intersecting, at an angle, at the central axis O of the continuum structure can cause the continuum structure to be more stable and driven reliably, and the stability of the structure is also higher. The connecting line AA and the connecting line BB intersect at an angle deviating from the central axis O of the continuum structure, such that it is easier for the continuum structure to bend toward the side where the flexible structural bones are less or no flexible structural bone is distributed.

Figure 7A:
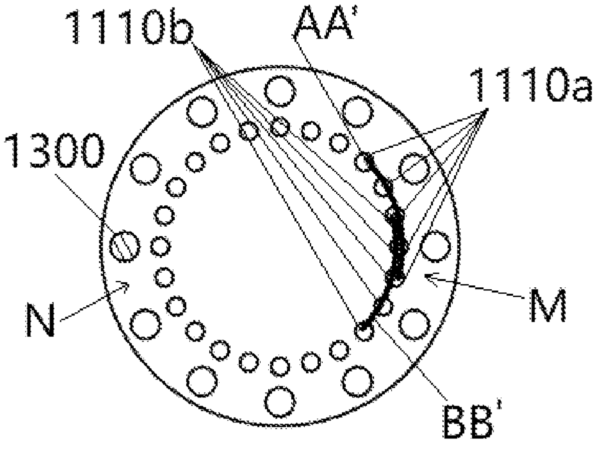
FIG. 7(*a*) shows a schematic diagram of projection of the flexible structural bones of the continuum structure along an axial direction according to other embodiments of the present disclosure.
Figure 7B:
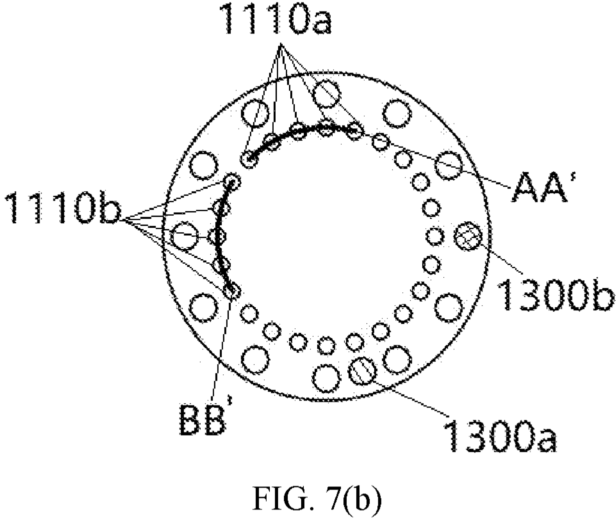
Figure 7C:
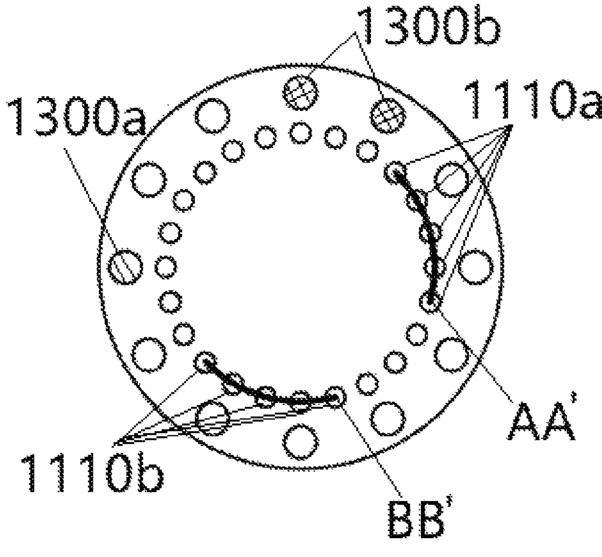

FIG. 7(*a*)-FIG. 7(*c*) show schematic diagrams of different projections of the flexible structural bones of the continuum structure along the axial direction according to some embodiments of the present disclosure. In some embodiments, as shown in FIG. 7(*a*)-FIG. 7(*c*), a plurality of flexible structural bones 1110*a* form a curve AA', and a plurality of flexible structural bones 1110*b* form a curve BB'. For example, curve AA' may be an arc formed by two flexible structural bones 1110*a*, and curve BB' may be an arc formed by two flexible structural bones 1110*b*, as shown in FIG. 7(*a*)-FIG. 7(*c*). It should be understood that curve AA' may be an arc formed by three or more flexible structural bones 1110*a*, and curve BB' may be an arc formed by three or more flexible structural bones 1110*b*. It should be understood that forming an arc may facilitate stable and controllable driving of the flexible structural bones. In some embodiments, curves AA' and BB' can also be irregular curves.

Curve AA' and curve BB' may include at least one of the following distributions: curve AA' partially overlaps with curve BB' (refer to FIG. 7(*a*) shown), curve AA' is adjacent to curve BB' (refer to FIG. 7(*b*) shown), curve AA' is opposite to curve BB', curve AA' and curve BB' are spaced apart along the circumference (refer to FIG. 7(*c*) shown), curve AA' is an arc, or curve BB' is an arc.

In some embodiments, the connecting structure 1100*a* may include a plurality of flexible structural bones 1110*a*, the connecting structure 1100*b* may include one flexible structural bone 1110*b*, and the plurality of flexible structural bones 1110*a* form a line AA or a curve AA'. The projection of the flexible structural bone 1110*b* along the axial direction of the continuum structure overlaps, is adjacent to, or opposite to the projection of the connecting line AA or the curve AA' along the axial direction.

Figure 8A:
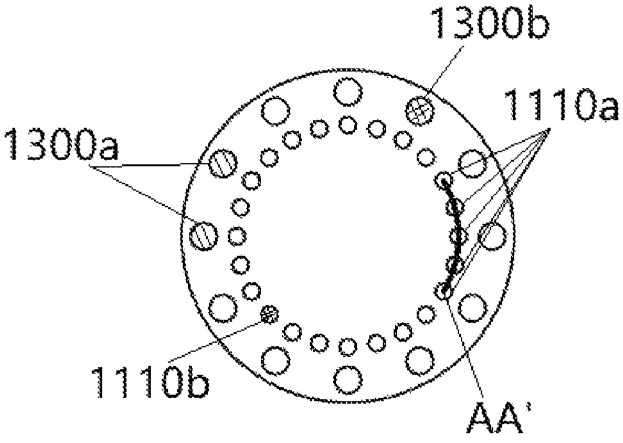
FIG. 8(*a*) shows a schematic diagram of projection of the flexible structural bones of the continuum structure along an axial direction according to other embodiments of the present disclosure.
Figure 8B:
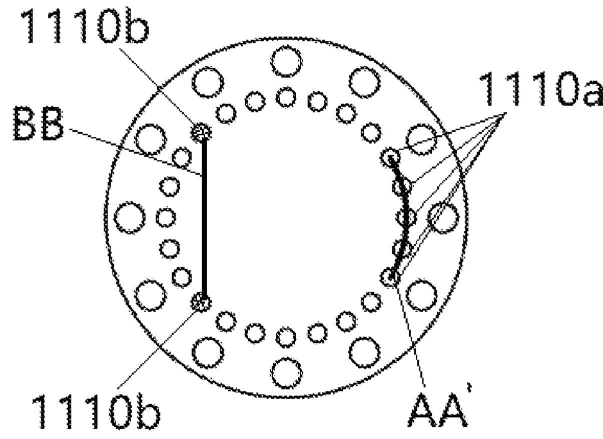

Similarly, the connecting structure 1100*a* may include one flexible structural bone 1110*a*, the connecting structure 1100*b* may include a plurality of flexible structural bones 1110*b*, and the plurality of flexible structural bones 1110*b* form a connecting line BB or a curve BB'. The projection of the flexible structural bone 1110*a* along the axial direction of the continuum structure and the projection of the connecting line BB or the curve BB' along the axial direction can overlap, be spaced apart in the circumferential direction, or be adjacent to each other. FIG. 8(*a*) and FIG. 8(*b*) respectively show schematic diagrams of different projections of the flexible structural bones of the continuum structure along the axial direction according to some embodiments of the present disclosure. As shown in FIG. 8(*a*), a plurality of flexible structural bones 1110*a* form a curve AA', and the projection of the flexible structural bones 1110*b* along the axial direction of the continuum structure is, along the circumferential direction, spaced apart from the projection of the curve AA' along the axial direction.

In some embodiments, the connecting structure 1100*a* may include a plurality of flexible structural bones 1110*a*, the connecting structure 1100*b* may include a plurality of flexible structural bone 1110*b*, and the plurality of flexible structural bones 1110*a* form a connecting line AA or a curve AA'. The plurality of flexible structural bones 1110*b* form a connecting line BB or a curve BB'. The connecting line AA or the curve AA' may partially overlap with, intersect with, be adjacent to, or be circumferentially spaced apart from the connecting line BB or the curve BB'. As shown in FIG. 8(*b*), a plurality of flexible structural bones 1110*a* form a curve AA', a plurality of flexible structural bones 1110*b* (for example, two flexible structural bones 1110*b*) form a connecting line BB, and the curve AA' and the connecting line BB are circumferentially spaced apart and provided oppositely. It should be understood that a plurality of flexible structural bones 1110*a* can form a connecting line AA, and a plurality of flexible structural bones 1110*b* can form a curve BB'.

Figure 9A:
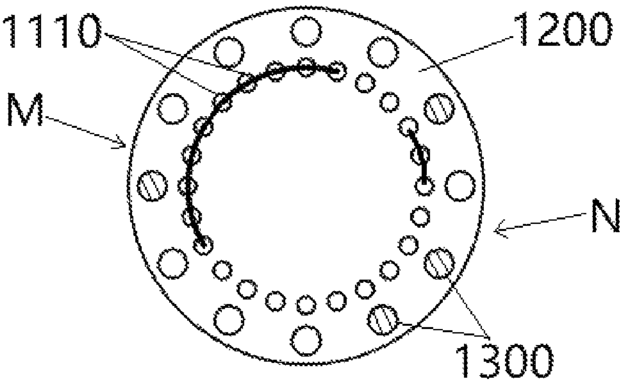
FIG. 9(*a*) shows a schematic diagram of projection of the flexible structural bones of the continuum structure along an axial direction according to other embodiments of the present disclosure.
Figure 9B:
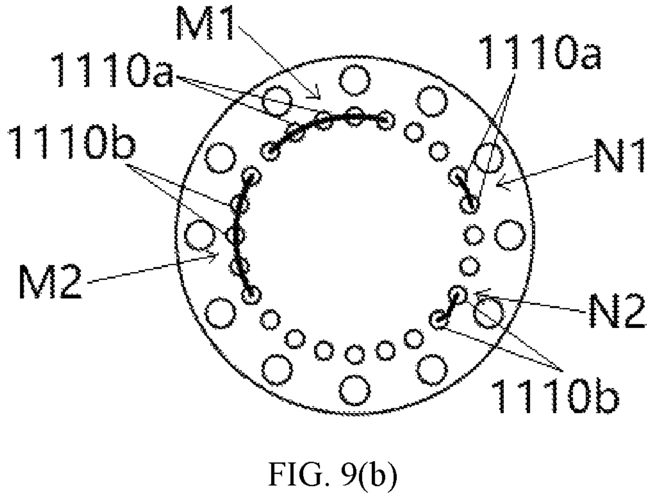
Figure 9C:
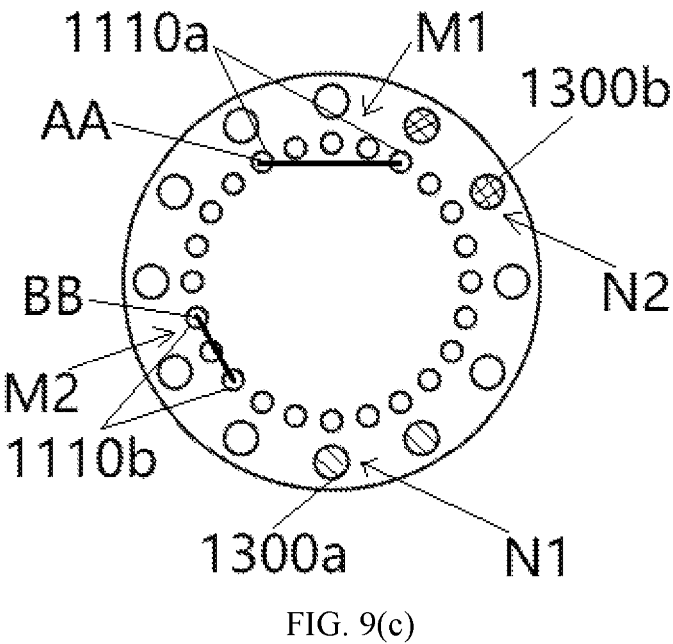

FIG. 9(*a*)-FIG. 9(*c*) respectively show schematic diagrams of different projections of the flexible structural bones of the continuum structure along the axial direction according to some embodiments of the present disclosure. In some embodiments, as shown in FIG. 9(*a*), the projection of one or more flexible structural bones 1110 along the axial direction of the continuum structure can form a high-density distribution area M and/or a low-density distribution area N. It should be understood that the number of flexible structural bone in the high-density distribution area M may be greater than the number of flexible structural bone in the low-density distribution area N. Alternatively, the distribution interval of the flexible structural bones in the high-density distribution area M may be smaller than the distribution interval of the flexible structural bones in the low-density distribution area N.

In some embodiments, no flexible structural bone is provided in the low-density distribution area N. Those skilled in the art can understand that multiple high-density distribution areas M and multiple low-density distribution areas N can be included, and the high-density distribution area M and the low-density distribution area N are relative concepts, and the division is not absolute and can be adjusted according to practical application. For example, as shown in FIG. 9(*a*), the high-density distribution area M may refer to the upper left semicircle area, while the low-density distribution area N refers to the lower right semicircle area.

It should be understood that the high-density distribution area M or the low-density distribution area N may be one or more arc-shaped areas or one or more rectangular areas or one or more irregular areas along the circumference of the spacer disc 1200. The high-density distribution area M and the low-density distribution area N may be two adjacent areas, or two spaced areas, or at least a part of the high-density distribution area M is opposite to at least a part of the low-density distribution area N. The high-density distribution area M and the low-density distribution area N may form a complete circumference of the spacer disc 1200, or may form an incomplete circumference of the spacer disc 1200 (refer to FIG. 9(*a*)). For example, as shown in FIG. 9(*b*), a plurality of flexible structural bones 1110*a* can form a high-density distribution area M1 and a low-density distribution area N1, and a plurality of flexible structural bones 1110*b* can form a high-density distribution area M2 and a low-density distribution area N2. The high-density distribution area M1 and the high-density distribution area M2 may be adjacent, opposite, circumferentially spaced apart, or may at least partially or completely overlap. Similarly, the low-density distribution area N1 and the low-density distribution area N2 may be adjacent, opposite, circumferentially spaced apart, or may at least partially or completely overlap. The low-density distribution area N1 and the low-density distribution area N2 can be connected to form a larger low-density distribution area, as shown in the lower right semicircle in FIG. 9(*b*) or the lower semicircle in FIG. 9(*c*). In the low-density distribution area N1 and the low-density distribution area N2, flexible structural bones may not be provided, as shown in FIG. 9(*c*). It should be understood that the flexible structural bones 1110*c* of a plurality of additional connecting structures can also form a high-density distribution area M and a low-density distribution area N together with the flexible structural bone 1110*a* or the flexible structural bone 1110*b*, or independently form a high-density distribution area and a low-density distribution area.

In some embodiments, one or more flexible structural bones 1110*a* and one or more flexible structural bones 1110*b* may only form a high-density distribution area M (such as M1 or M2), or form a high-density distribution area M and a low-density distribution area N (for example, N1 or N2). For example, the axial projections of a plurality of flexible structural bones 1110*a* may be distributed along the same circle, or along part of the same circle, or along different circles. In this way, the distribution is asymmetrical along the circumferential direction of the spacer disc 1200, so that the continuum structure can better bend toward the direction of the low-density distribution area where less flexible structural bones are distributed. In some embodiments, the projections of the plurality of flexible structural bones 1110*a* and the plurality of flexible structural bones 1110*b* along the axis direction form a semicircle. For example, a plurality of flexible structural bones 1110*a* may be distributed along a quarter of the circle, and a plurality of flexible structural bones 1110*b* may be distributed along a quarter of the circle adjacent to the plurality of flexible structural bones 1110*a*. Alternatively, the plurality of flexible structural bones 1110*a* and the plurality of flexible structural bones 1110*b* may be evenly staggered along the semicircle. The continuum structure 1000 may include one or more serially connected connecting structures 1100*a* and one or more serially connected connecting structures 1100*b* that are periodically staggered. By pushing or pulling the flexible structural bone 1110*a* and the flexible structural bone 1110*b*, the continuum structure bends toward the side where no flexible structural bone is distributed, achieving stable and controllable bending in a specific direction.

In some embodiments, as shown in FIG. 1, the continuum structure 1000 may include one or more driving structural bones 1300. One or more driving structural bones 1300 slide through the plurality of spacer discs 1200 in the axial direction, and the first end thereof is fixedly connected to the spacer disc 1200 located at the farthest end. The plurality of connecting structures 1100 are driven to bend by pushing or pulling one or more driving structural bones 1300. In some embodiments, the second end of one or more driving structural bones 1300 extends through a plurality of spacer discs 1200 along the proximal end, and is used for fixed connection with the driving mechanism, and a plurality of connected structures are driven to bend by the driving mechanism pushing or pulling one or more driving structural bone 1300. It should be understood that the driving mechanism may include a linear motion mechanism, such as a screw nut structure or a double-ended screw structure, etc., and the driving mechanism linearly pushes or pulls one or more driving structural bones 1300 to drive the continuum structure to bend.

In some embodiments, as shown in FIG. 9(*a*), in the projection of the flexible structural bones 1110 of a plurality of connecting structures 1100 along the axial direction of the continuum structure, the number of the one or more driving structural bones 1300 in the low-density distribution area N is larger than that in the high-density distribution area M. It should be understood that one or more driving structural bones 1300 may also be distributed only in the low-density distribution area. Disposing more driving structural bones in the low-density distribution area N allows finer and more stable control (such as bending angle, direction, and so on) of the bending of the continuum structure.

For example, a plurality of driving structural bones 1300 are distributed along the same circle, or circumferentially distributed along part of the same circumference (refer to FIG. 9(*a*)), or distributed along different circumferences. In some embodiments, one or more driving structural bones 1300 may include driving structural bones 1300 distributed in the middle of the low-density distribution area N. For example, as shown in FIG. 7(*a*), the flexible structural bone 1110*a* and the flexible structural bone 1110*b* form a high-density distribution area M (for example, a right semicircle area) and a low-density distribution area N (for example, a left semicircle area), no flexible structural bone is distributed in the low-density distribution area, and the driving structural bone 1300 may include the driving structural bone distributed in the middle of the low-density distribution area N. Stable and controllable driving is realized through the driving structural bone 1300 distributed in the middle of the corresponding low-density distribution area.

In some embodiments, a plurality of driving structural bones 1300 may be symmetrically distributed along the circumference of the spacer disc 1200. For example, the projections of a plurality of flexible structural bones along the axial direction form a high-density distribution area M and a low-density distribution area N, and a plurality of driving structural bones 1300 are distributed in the high-density distribution area M and the low-density distribution area N, can be symmetrically distributed with respect to the center of spacer disc 1200, or can be non-centrosymmetrically distributed. In some embodiments, as shown in FIG. 9(*a*), a plurality of driving structural bones 1300 may be asymmetrically distributed along the circumference of the spacer disc 1200. For example, the circumferential asymmetric distribution may include, but is not limited to, that a plurality of driving structural bones 1300 may be respectively distributed along different inner contour lines or inner circumference lines in the high-density distribution area M and the low-density distribution area N; or a plurality of driving structural bones 1300 may be distributed along the same inner contour line or inner circumference line (refer to FIG. 9(*a*)), and the number thereof in the low-density distribution areas N is greater than that in the high-density distribution areas M; or a plurality of driving structural bones 1300 are distributed at different intervals to form a circumferential asymmetric distribution along the spacer disc 1200. Through the symmetrical or asymmetrical distribution of the driving structural bones 1300, one or more flexible structural bones 1300 in different distributions can be driven to achieve bending in multiple directions. According to actual needs, the number of flexible structural bones can be reduced in a desired bending direction, and the number of unnecessary driving structural bones 1300 can be reduced, so as to realize the miniaturization of the continuum structure.

In some embodiments, as shown in FIG. 9(*c*), at least two flexible structural bones 1110*a* of the plurality of flexible structural bones 1110*a* form a connecting line AA, and at least two flexible structural bones 1110*b* of the plurality of flexible structural bones 1110*b* form a connecting line BB, one or more driving structural bones 1300 include driving structural bones 1300 passing through positions of corresponding perpendicular bisectors of the connecting line AA and/or the connecting line BB on the spacer disc 1200 (for example, one driving structural bone 1300*a* may pass through the position of the perpendicular bisector of the connecting line AA, and one driving structural bone 1300*b* can pass through the position of the perpendicular bisector of the connecting line BB). It should be understood that the low-density distribution area N may include an area corresponding to the perpendicular bisector formed by the connecting line AA and/or the connecting line BB, one or more driving structural bones 1300 are located in the low-density distribution area N, and a portion of the driving structural bones 1300 pass through the position of the perpendicular bisector of the corresponding connecting line AA and/or the connecting line BB on the spacer disc 1200. In some embodiments, a plurality of flexible structural bones 1110*a* form a curve AA', a plurality of flexible structural bones 1110*b* form a curve BB', and the low-density distribution area N may include an area corresponding to the arc of the curve AA' and/or the curve BB'. One or more driving structural bones 1300 are located in the low-density distribution area N, and a portion of the driving structural bones 1300 are located at positions of the arc centerline of curve AA' and/or curve BB'. Those skilled in the art should understand that the above distribution of the driving structural bones 1300 is only an example, and the present disclosure is not limited thereto, and may also include other cases of the driving structural bones 1300 being distributed asymmetrically or symmetrically.

Figure 10:
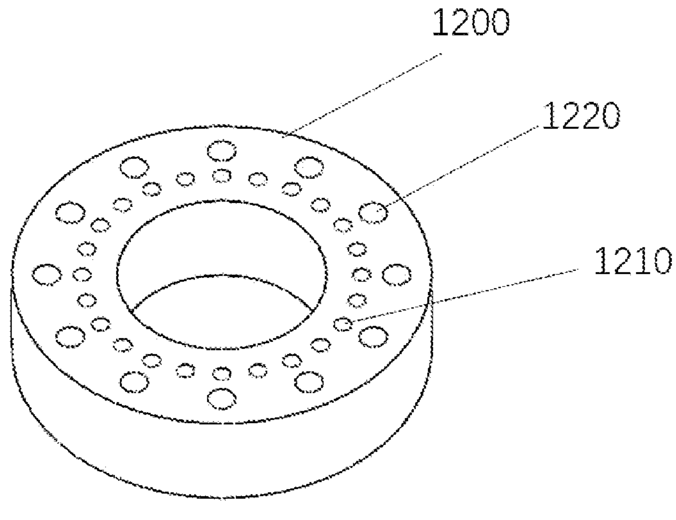
FIG. 10 shows a structural schematic diagram of a spacer disc of the continuum structure according to some embodiments of the present disclosure.

FIG. 10 shows a structural schematic diagram of a spacer disc 1200 of the continuum structure 1000 according to some embodiments of the present disclosure. In some embodiments, as shown in FIG. 10, a plurality of spacer discs 1200 may include one or more mounting holes 1210 distributed along a first inner contour line or inner circumference line (for example, an inner perimeter line) and one or more mounting holes 1220 distributed along a second contour line or inner circumference line, and the first inner contour line or inner circumference line are radially spaced from the second inner contour line or inner circumference line. One or more flexible structural bones 1110 are fixedly connected to corresponding mounting holes 1210 of adjacent spacer discs 1200, and one or more driving structural bones 1300 are disposed in corresponding mounting holes 1220 of a plurality of spacer discs 1200 by sliding through therein. In some embodiments, as shown in FIG. 3, the first inner contour line or inner circumference line is at a distance D1 from the central axis O of the continuum structure, and the second inner contour line or inner circumference line is at a distance D2 from the central axis O of the continuum structure, and the distance D2 is greater than the distance D1. For example, the first inner contour line or inner circumference line can be a first circle, the second inner contour line or inner perimeter line can be a second circle, a plurality of mounting holes 1210 are distributed along the first circle, a plurality of mounting holes 1220 are distributed along the second circle, and the first circle and the second circle are radially spaced apart. In some embodiments, the first inner contour line or inner perimeter line and the second inner contour line or inner perimeter line may also be on the same circle line. For example, the first inner contour line or inner perimeter line can be distributed in a first area of a circumference, the second inner contour line or inner perimeter line can be distributed in a second area of the same circle, the first area is adjacent to the second area or at least partially opposite.

In some embodiments, the flexible structural bone 1110 and the driving structural bone 1300 may include, but are not limited to, thin rods or thin tubes made of deformable material, such as nickel-titanium alloy material. It should be understood that the flexible structural bone 1110 may also be a biocompatible deformable polymer material.

Figure 11:
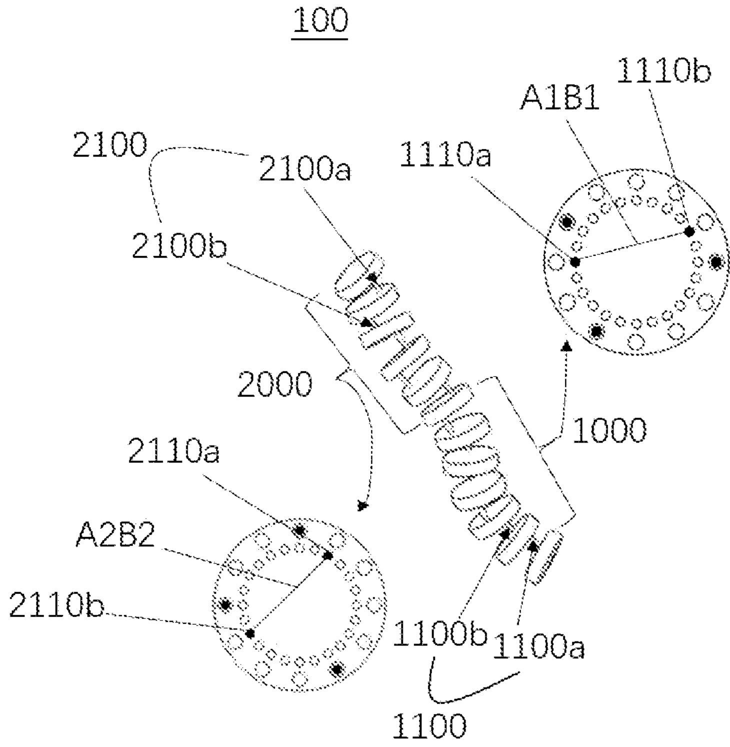
FIG. 11 shows a structural schematic diagram of a continuum instrument according to some embodiments of the present disclosure.

FIG. 11 shows a structural schematic diagram of a continuum instrument 100 according to some embodiments of the present disclosure. As shown in FIG. 11, the continuum instrument 100 may include a plurality of serially connected continuum structures. In some embodiments, as shown in FIG. 11, the plurality of continuum structures of the continuum instrument 100 may include a continuum structure 1000 and a continuum structure 2000 connected in series with the continuum structure 1000. The plurality of connecting structures 1100 of the continuum structure 1000 include connecting structure 1100*a* and connecting structure 1100*b* connected in series, the connecting structure 1100*a* may include one flexible structural bone 1110*a*, the connecting structure 1100*b* may include one flexible structural bone 1110*b*, and the flexible structural bone 1110*a* and the flexible structural bone 1110*b* is staggered by a first included angle along the circumferential direction of the spacer disc, and projections of the flexible structural bone 1110*a* and the flexible structural bone 1110*b* along the axial direction of the continuum structure form a projected connecting line A1B1.

As shown in FIG. 11, a plurality of connecting structures 2100 of the continuum structure 2000 may include connecting structure 2100*a* and connecting structure 2100*b* connected in series. The connecting structure 2100*a* may include one flexible structural bone 2110*a*, the connecting structure 2100*b* may include one flexible structural bone 2110*b*, the flexible structural bone 2110*a* and the flexible structural bone 2110*b* are staggered by a second included angle along the circumference of the spacer disc, and projections of the flexible structural bone 2110*a* and the flexible structural bone 2110*b* along the axial direction of the continuum structure form a projected connecting line A2B2. The projected connecting line A1B1 and the projected connecting line A2B2 include at least one of the following distributions: projected connecting line A1B1 and projected connecting line A2B2 intersect at an angle at the central axis O of the continuum structure, the projected connecting line A1B1 passes through the central axis O of the continuum structure and intersect at an angle with the projected connecting line A2B2 outside the central axis O of the continuum structure, the projected connecting line A1B1 and the projected connecting line A2B2 deviate from the central axis O of the continuum structure and intersect, or the projected connecting line A1B1 and the projected connecting line Lines A2B2 deviate from the central axis O of the continuum structure and intersect on their extended lines. In some embodiments, the first included angle is equal to the second included angle, but the projected connecting line A1B1 and the projected connecting line A2B2 form an included angle. For example, the continuum structure 1000 and the continuum structure 2000 are structurally the same, but connected in series with a staggered angle along the circumferential direction of the continuum instrument. Those skilled in the art can understand that although FIG. 11 only shows two types of continuum structures 1000, 2000, a plurality of continuum structures may also include one or more other types of continuum structures.

In some embodiments, an easy-to-bend direction of the continuum structure 1000 is different from an easy-to-bend direction of the continuum structure 2000. It should be understood that, in the present disclosure, the easy-to-bend direction refers to the direction in which the continuum structure as a whole or the connecting structure is most easily to bend. The easy-to-bend direction of the continuum structure is the direction where a plurality of connecting structures contained in the continuum structure as a whole reflect the easy-to-bend. In some embodiments, the easy-to-bend direction includes a fan-shaped area centered on the central axis of the continuum structure or the connecting structure, and the easy-to-bend direction may refer to the central direction of the fan-shaped area. In some embodiments, the easy-to-bend direction of the continuum structure refers to a central direction of the low-density distribution area formed by the flexible structural bones of the plurality of connecting structures along the axial direction and opposite to the high-density distribution area and. For example, the continuum structure includes a fan-shaped area that does not distribute flexible structural bones (such as flexible structural bones 1110*a*, 1110*b*, 2110*a*, 2110*b*), and the easy-to-bend direction may refer to a central direction of the fan-shaped area. If there are multiple fan-shaped areas where flexible structural bones are not distributed, the easy-to-bend direction may refer to a central direction of the largest fan-shaped area. It should be understood that, as shown in FIG. 11, the easy-to-bend direction of the continuum structure 1000 is different from the easy-to-bend direction of the continuum structure 2000.

In some embodiments, the continuum structure 1000 and the continuum structure 2000 have different easy-to-bend directions. For example, the easy-to-bend directions of the continuum structure 1000 and the continuum structure 2000 may be opposite, and the bending of the continuum structure 1000 and the continuum structure 2000 may form an "S" shape. It should be understood that the bending of the continuum structure 1000 and the continuum structure 2000 may also form waves or irregular curves, etc. It should be understood that the "S" shape presented by the bending can make the driving of the continuum instrument 100 more stable and controllable.

In some embodiments, the continuum structure 1000 and the continuum structure 2000 have different bending curvatures. For example, the bending curvature of the continuum structure 1000 may be greater than the bending curvature of the continuum structure 2000. Through different bending curvatures, the continuum instrument 100 can realize complex configurations, and can realize complex configurations controllably.

Figure 12:
FIG. 12 shows a structural schematic diagram of a continuum instrument according to other embodiments of the present disclosure.
Figure 12:
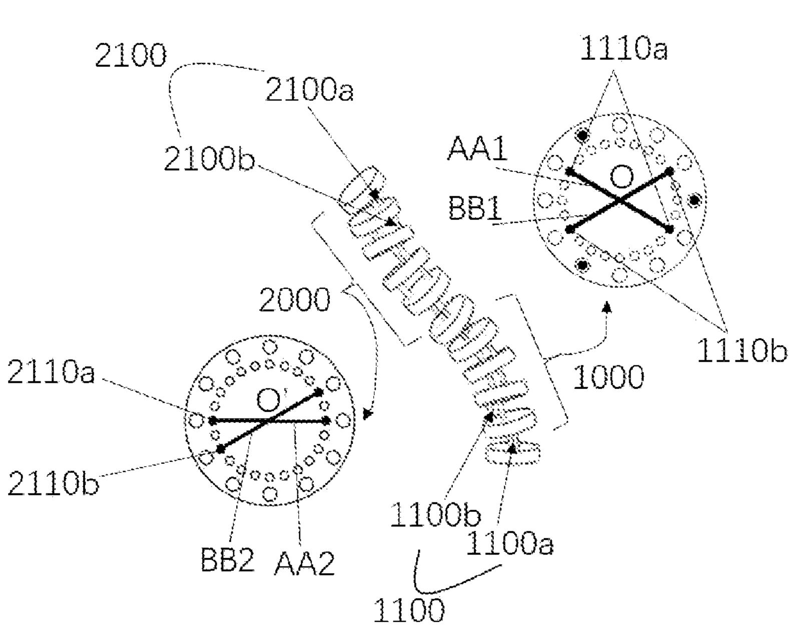

FIG. 12 shows a structural schematic diagram of a continuum instrument 200 according to some embodiments of the present disclosure. As shown in FIG. 12, a plurality of continuum structures of the continuum instrument 200 may include a continuum structure 1000 and a continuum structure 2000 connected in series with the continuum structure 1000. The plurality of connecting structures 1100 of the continuum structure 1000 include connecting structure 1100*a* and connecting structure 1100*b* connected in series, the connecting structure 1100*a* may include a plurality of (for example, two as shown in FIG. 12) flexible structural bones 1110*a*, and the connecting structure 1100*b* may include a plurality of (for example, two as shown in FIG. 12) flexible structural bones 1110*b*. A plurality of flexible structural bones 1110*a* form a connecting line AA1, and a plurality of flexible structural bones 1110*b* form a connecting line BB1. The connecting line AA1 and the connecting line BB1 may include at least one of the following distributions: the connecting line AA1 and the connecting line BB1 intersect at a first angle at the central axis O of the continuum structure 1000, the connecting line AA1 passes through the central axis O of the continuum structure 1000 and intersect at a first angle with the connecting line BB1 outside the central axis O of the continuum structure 1000, the connecting line AA1 and the connecting line BB1 deviate from the central axis O of the continuum structure and intersect at a first angle, or the connecting line AA1 and the connecting line BB1 deviate from the central axis O of the continuum structure and intersect on their extended lines.

As shown in FIG. 12, a plurality of connecting structures 2100 of the continuum structure 2000 include connecting structure 2100*a* and connecting structure 2100*b* connected in series. The connecting structure 2100*a* includes a plurality of (for example, two as shown in FIG. 12) flexible structural bones 2110*a*, and the connecting structure 2100*b* includes a plurality of (for example, two as shown in FIG. 12) flexible structural bones 2110*b*. A plurality of flexible structural bones 2110*a* form a connecting line AA2, and a plurality of flexible structural bones 2110*b* form a connecting line BB2. The connecting line AA2 and the connecting line BB2 may include at least one of the following distributions: the connecting line AA2 and the connecting line BB2 intersect at a second angle at the central axis O' of the continuum structure 2000, the connecting line AA2 passes through the central axis O' of the continuum structure 2000 and intersect at a second angle with the connecting line BB2 outside the central axis O' of the continuum structure 2000, the connecting line AA2 and the connecting line BB2 deviate from the central axis O' of the continuum structure 2000 and intersect at a second angle, or the connecting line AA2 and the connecting line BB2 deviate from the central axis O' of the continuum structure 2000 and intersect on their extended lines.

For example, as shown in FIG. 12, the connecting line AA1 and the connecting line BB1 may intersect at a first angle (for example, an obtuse angle formed between the connecting line AA1 and the connecting line BB1) at the central axis O of the continuum structure 1000, and the connecting line AA2 and the connecting line BB2 intersect at a second angle (for example, an obtuse angle formed between the connecting line AA2 and the connecting line BB2) at the central axis O' of the continuum structure 2000. Such continuum structure 1000 and continuum structure 2000 are more stable and controllable. The second angle may be greater than the first angle, and the bending curvature of the continuum structure 2000 is greater than that of the continuum structure 1000. The easy-to-bend direction of the continuum structure 1000 can be opposite to that of the continuum structure 2000, so that the continuum instrument 2000 can realize S-shaped bending. By adjusting the first angle and the second angle, the bending characteristic of the continuum instrument 200 can be easily changed.

In some embodiments, as shown in FIG. 12, the connecting line AA1 and the connecting line BB1 form a first included angle (for example, an obtuse angle formed between the connecting lines AA1 and BB1), and the connecting line AA2 and the connecting line BB2 form a second included angle (for example, the obtuse angle formed between the connecting lines AA2 and BB2). In some embodiments, the first included angle may be equal to the second included angle, but the first included angle and the second included angle are staggered by an angle along the circumferential direction. In this way, the continuum structure 2000 the continuum structure 1000 are structurally the same and are connected in series with a staggered angle along the circumferential direction of the continuum instrument.

It should be understood that the connecting line of the flexible structural bones (such as AA1 or BB1) in the continuum structure 1000 can be replaced by a curve, and the connecting line of the flexible structural bones (such as AA2 or BB2) in the continuum structure 2000 can also be replaced by a curve.

Figure 13:
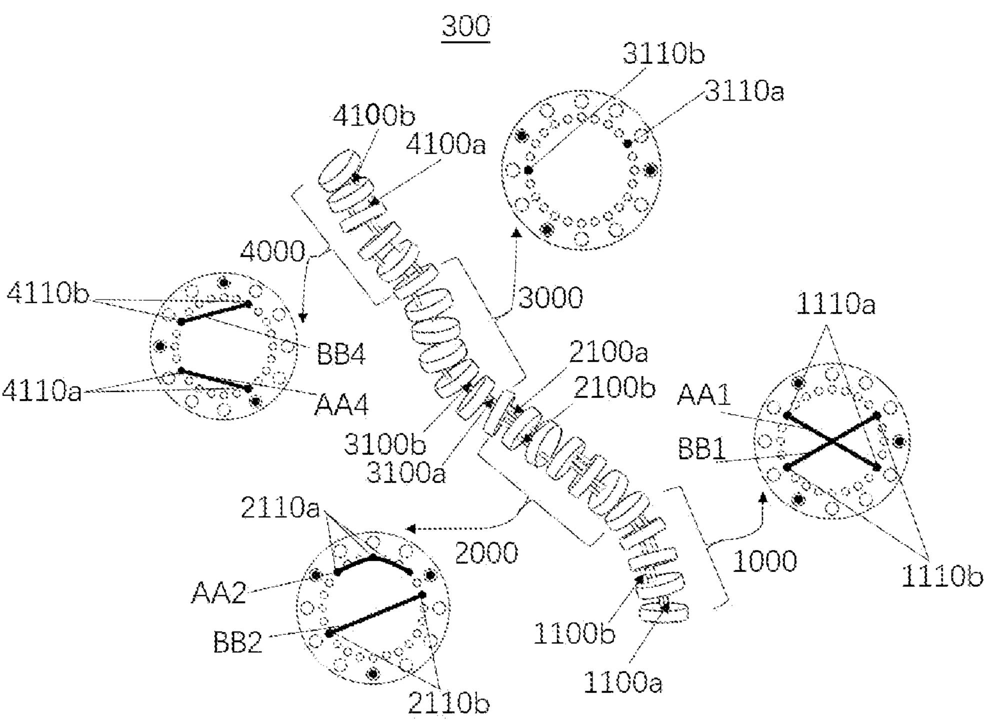
FIG. 13 shows a structural schematic diagram of a continuum instrument according to other embodiments of the present disclosure.

FIG. 13 shows a structural schematic diagram of a continuum instrument 300 according to some embodiments of the present disclosure. As shown in FIG. 13, continuum instrument 300 may include continuum structure 1000, continuum structure 2000, continuum structure 3000 and continuum structure 4000 connected in series. In some embodiments, at least two of the continuum structures 1000, 2000, 3000, and 4000 have different easy-to-bend directions. It should be understood that the continuum instrument can also include more continuum structures connected in series. For example, the connecting structure 1100*a* of the continuum structure 1000 may include two flexible structural bones 1110*a* forming a connecting line AA1, the connecting structure 1100*b* of the continuum structure 1000 may include two flexible structural bones 1110*b* forming a connecting line BB1, and the connecting line AA1 and the connecting line BB1 may intersect at the central axis. The connecting structure 2100*a* of the continuum structure 2000 may include three flexible structural bones 2110*a*, wherein the three flexible structural bones 2110*a* form an arc AA2. The connecting structure 2100*b* of the continuum structure 2000 may include two flexible structural bones 2110*b*, the two flexible structural bones 2110*b* form a connecting line BB2, and the arc line AA2 may be opposite to the connecting line BB2. The connecting structure 3100*a* of the continuum structure 3000 may include one flexible structural bone 3110*a*, the connecting structure 3100*b* of the continuum structure 3000 may include one flexible structural bone 3110*b*, and the projections of the flexible structural bone 3110*a* and the flexible structural bone 3110*b* along the axial direction are spaced apart. The connecting structure 4100*a* of the continuum structure 4000 may include two flexible structural bones 4110*a*, and the two flexible structural bones 4110*a* form a connecting line AA4. The connecting structure 4100*b* of the continuum structure 4000 may include two flexible structural bones 4110*b*, and the two flexible structural bones 4110*b* forms a connecting line BB4. The connecting line AA4 and the connecting line BB4 can intersect in the extending direction. The continuum instrument 300 can achieve complex, controllable configuration. For example, the continuum structures 1000, 2000, 3000 and 4000 have different easy-to-bend directions and can form a complex S shape. In addition, the continuum structure 3000 is easier to bend and has a smaller bending curvature, and can serve as a more flexible joint to realize finer control and manipulation.

It should be understood that the above is only an example, the present disclosure is not limited thereto, and the plurality of continuum structures 1000, 2000, 3000, and 4000 of the continuum instrument 300 may also be other types of continuum structures.

In some embodiments, a continuum instrument (such as the continuum instrument 100, 200 or 300) may further include at least one rigid connector (not shown in the Figure). A rigid connector may be disposed between at least one pair of adjacent continuum structures of a plurality of continuum structures (for example, continuum structures 1000, 2000, 3000 or 4000). It should be understood that mutual interference between multiple continuum structures can be avoided through the rigid connector. In addition, the rigid connector can also give appropriate rigidity to the continuum instrument, so that the continuum instrument can enter deeper and curved complex cavities, and can avoid the incapability of accurately and stably driving caused by the excessive flexibility of a plurality of continuum structures.

In some embodiments, the continuum instrument (such as, the continuum instrument 100, 200 or 300) may include a plurality of driving structural bones, one end of the plurality of driving structural bones is fixedly connected with a distal spacer disc of the plurality of continuum structures, and the other end is used to receive drive to independently drive the plurality of continuum structures to steer.

Figure 14:
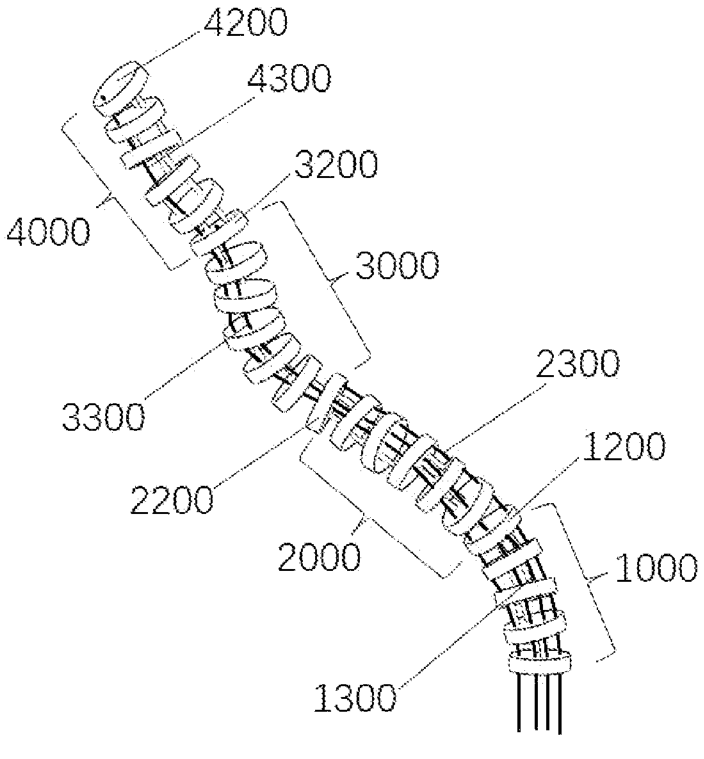
FIG. 14 shows a structural schematic diagram of a distribution of driving structural bones of a continuum instrument according to other embodiments of the present disclosure.

FIG. 14 shows a structural schematic diagram of a distribution of driving structural bones of a continuum instrument according to some embodiments of the present disclosure. In some embodiments, as shown in FIG. 14, a plurality of driving structural bones may at least include one or more driving structural bones 1300 and one or more driving structural bones 2300. A first end of one or more driving structural bones 1300 is fixedly connected to a distal spacer disc 1200 of a continuum structure 1000 of a plurality of continuum structures. A first end of one or more driving structural bones 2300 is fixedly connected to a distal spacer disc 2200 of a continuum structure 2000 of the plurality of continuum structures. In some embodiments, as shown in FIG. 14, a plurality of driving structural bones may also include one or more driving structural bones 3300 and one or more driving structural bones 4300. A first end of one or more driving structural bones 3300 is fixedly connected to a distal spacer disc 3300 of a continuum structure 3000 of the plurality of continuum structures. A first end of one or more driving structural bones 4300 is fixedly connected to a distal spacer disc 4200 of a continuum structure 4000 of the plurality of continuum structures. FIG. 14 only shows the situation where one driving structural bone 1300, one driving structural bone 2300, one driving structural bone 3300 and one driving structural bone 4300 are included, however it should be understood that the respective continuum structures may also include two, three or more driving structural bones. Through driving structural bones, respective continuum structures 1000, 2000, 3000, 4000 can be independently controlled, thus improving the controllability, flexibility and operability of the continuum instrument.

Figure 15A:
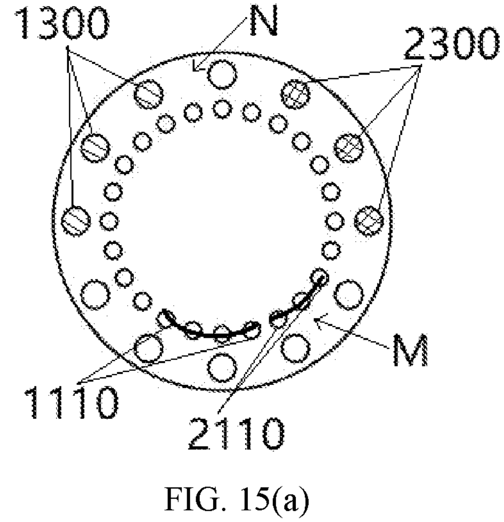
FIG. 15(*a*) shows a schematic diagram of projection of driving structural bones of the continuum instrument along an axial direction according to other embodiments of the present disclosure.
Figure 15B:
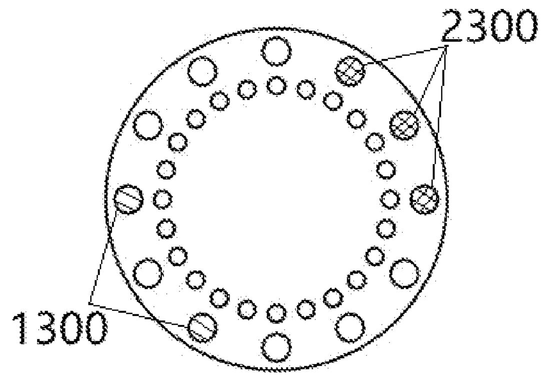
Figure 15C:
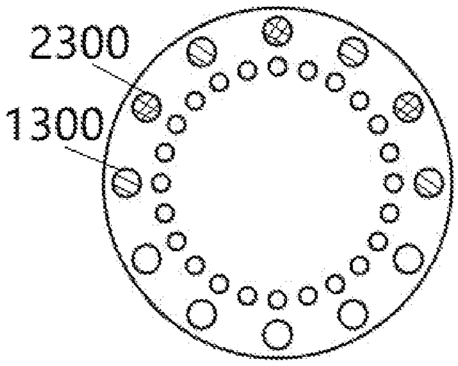

FIG. 15(*a*)-FIG. 15(*c*) respectively show schematic diagrams of different projections of the driving structural bones of the continuum instrument along the axial direction according to some embodiments of the present disclosure. In some embodiments, a plurality of driving structural bones may include a plurality of driving structural bones 1300 and a plurality of driving structural bones 2300. It should be understood that the plurality of driving structural bones 1300 may be distributed symmetrically (as shown in FIG. 15(*a*)) or asymmetrically along the circumferential direction of the spacer disc. It should be understood that the circumferentially symmetrical distribution may be circumferentially axisymmetrical or centrosymmetrical distribution. Alternatively, the plurality of driving structural bones 2300 are distributed symmetrically (as shown in FIG. 15(*a*)) or asymmetrically along the circumferential direction of the spacer disc. Alternatively, the plurality of driving structural bones 1300 and the plurality of driving structural bones 2300 are distributed symmetrically (as shown in FIG. 15(*a*)) or asymmetrically (as shown in FIG. 15(*b*)) along the circumferential direction of the spacer disc. Alternatively, the driving structural bones 1300 and the driving structural bones 2300 are staggered (as shown in FIG. 15(*c*)). It should be understood that the symmetrical distribution of the driving structural bones along the circumferential direction of the spacer disc can make the driving of a plurality of continuum structures more stable and controllable.

In some embodiments, as shown in FIG. 15(*a*), in the projections of one or more driving structural bones 1300 and one or more driving structural bones 2300 along the axial direction of the continuum structure, the number of the driving structural bones in the low-density distribution area N is larger than those in the high-density distribution area. In this way, by driving the structural bone, the bending (for example, bending toward the easy-to-bend direction) of the continuum instrument can be more conveniently and finely controlled. For example, the axial projections of one or more flexible structural bones 1110 and one or more flexible structural bones 2110 may be distributed in the high-density distribution area M (for example, the lower semicircle), and the axial projections of one or more driving structural bones 1300 and one or more driving structure bones 2300 may be distributed in the low-density distribution area N (for example, the upper semicircle), so as to drive the continuum structures 1000 and 2000 to bend toward the side of the low-density distribution area N. It should be understood that the above distribution of the flexible structural bone and the driving structural bone is only an example, and the present disclosure is not limited thereto.

In some embodiments, the cross-sectional dimensions (for example, radius) of the plurality of serially connected continuum structures decrease one by one from the proximal end to the distal end along the axial direction of the continuum structures. For example, a plurality of continuum structures may include continuum structure 1000, continuum structure 2000, continuum structure 3000 and continuum structure 4000 which are connected in series from the proximal end to the distal end. The cross-sectional dimension of the continuum structure 1000 at the proximal end is a first cross-sectional dimension, the cross-sectional dimension of the continuum structure 2000 is a second cross-sectional dimension, the cross-sectional dimension of the continuum structure 3000 is a third cross-sectional dimension, and the cross-sectional dimension of the continuum structure 4000 is a fourth cross-sectional dimension. The first cross-sectional dimension is larger than the second cross-sectional dimension, the second cross-sectional dimension is larger than the third cross-sectional dimension, and the third cross-sectional dimension is larger than the fourth cross-sectional dimension. It should be understood that the cross-sectional dimension may be the cross-sectional dimension of the spacer disc of the respective continuum structure. It should be understood that the cross-sectional dimensions of the plurality of serially connected continuum structures decrease one by one from the proximal end to the distal end, so that the distal end of the continuum instrument can enter the narrow lumen at a deep location without injuring the lumen tissue, and can be better adapted to complex lumen and complex operation tasks.

In some embodiments, the driving structural bones (for example, the driving structural bones 1300) of the proximal continuum structure (for example, the continuum structure 1000) of the plurality of continuum structures are distributed outside of the driving structural bone (for example, the driving structural bone 2300, 3300 or 4300) of the distal continuum structure (for example, the continuum structure 2000, 3000 or 4000). For example, the cross-sectional dimension of the proximal continuum structure 1000 is larger than that of the distal continuum structure 2000 (or the continuum structure 3000, 4000), so that the driving structural bone 1300 can be distributed outside the driving structural bone 2300. Alternatively, the cross-sectional dimension of the proximal continuum structure 1000 is the same as that of the distal continuum structure 2000 (or the continuum structure 3000, 4000), the driving structural bones 1300 are distributed on a third inner contour line or a third inner circumference line, the driving structural bones

2300 are distributed on a fourth inner contour line or a fourth inner circumference line, the third inner contour line or the third inner circumference line is outside the fourth inner contour line or the fourth inner circumference line and farther away from the central axis, so that the driving structural bone 1300*s* are distributed outside the driving structural bones 2300.

Figure 16:
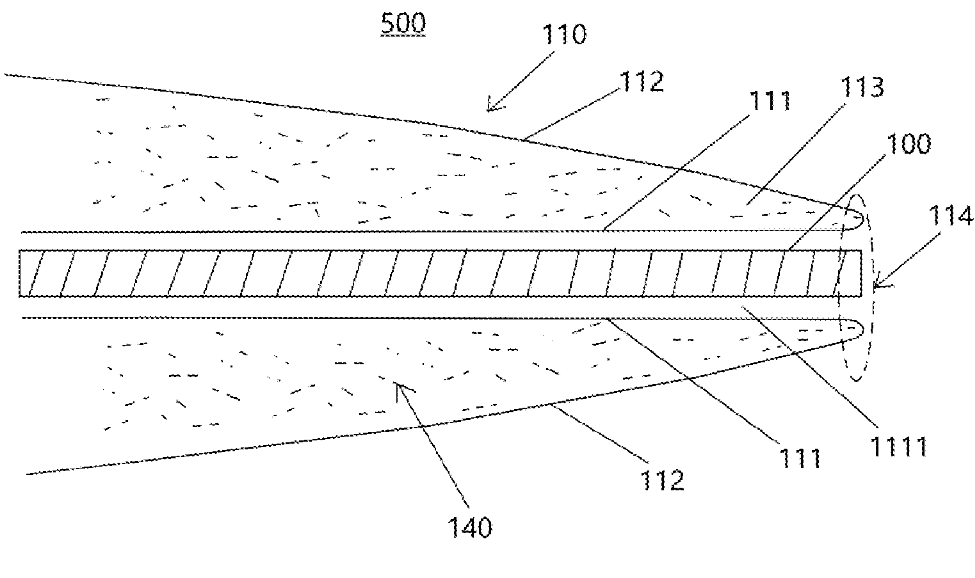
FIG. 16 shows a structural schematic diagram of a distal portion of the growable continuum instrument according to some embodiments of the present disclosure.

FIG. 16 shows a structural schematic diagram of a distal portion of the growable continuum instrument 500 according to some embodiments of the present disclosure. As shown in FIG. 16, the growable continuum instrument 500 may include a growable tube 110 and the continuum instrument 100 (or continuum instrument 200, 300) located in an inner channel 1111 of the growable tube 110. The continuum instrument 100 (or the continuum instrument 200, 300) may comprise one or more serially connected continuum structures (e.g., the continuum structures 1000, 2000, 3000, 4000).

Figure 17:
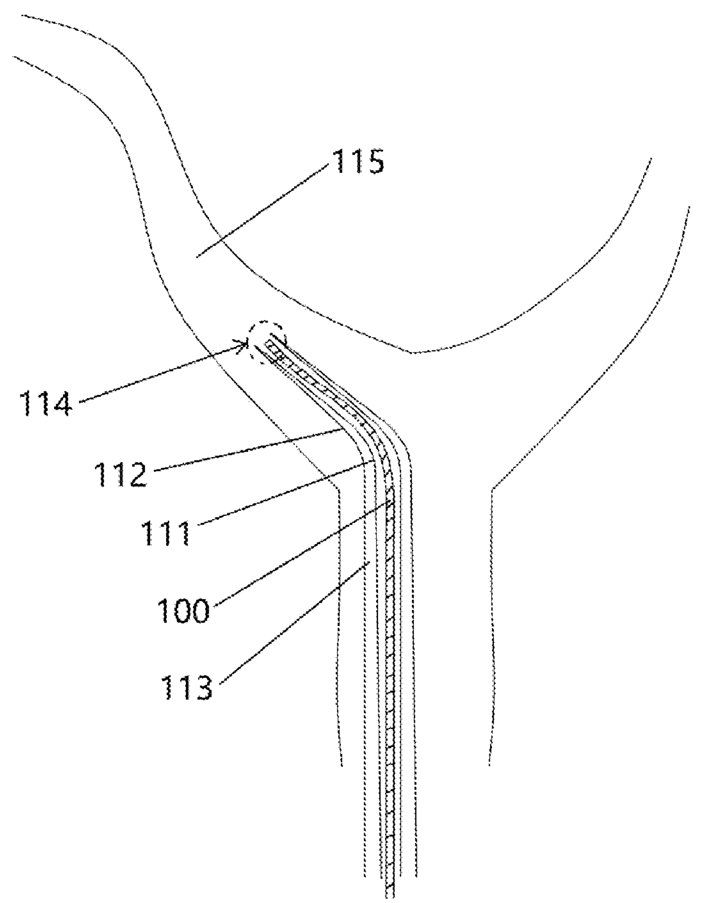
FIG. 17 shows a structural schematic diagram of a distal portion of the growable continuum instrument located within a lumen according to some embodiments of the present disclosure.

FIG. 17 shows a structural schematic diagram of a distal portion of a growable continuum instrument 500 positioned within a lumen 115 (e.g., blood vessel, trachea, esophagus, vagina, intestinal tract, etc.) in a body (e.g., in a human body or an animal body) according to some embodiments of the present disclosure. The growable continuum instrument 500 may enter the lumen 115 through an opening (for example, an incision or a natural opening). The growable tube 110 may comprise flexible material including for example, but not limited to, plastic, rubber, etc., for example, low density polyethylene, silicon-containing polymers, or fluoropolymer. The flexible growable tube 110 can avoid injury to the lumen 115. In some embodiments, the cross-section of the growable tube 110 may be circular, elliptical, rectangular, polygonal, or other shape.

In some embodiments, as shown in FIG. 16, the growable tube 110 includes an inner layer 111, an outer layer 112, and a fluid chamber 113 between the inner layer 111 and the outer layer 112. The fluid chamber 113 is used to accommodate fluid 140. The growable tube 110 also includes a turnable region 114 at the distal end, the inner layer 111 and the outer layer 112 are connected and turnable in the turnable region 114.

In some embodiments, the radial dimension of the proximal end of the outer layer 112 is larger than the radial dimension of the distal end of the outer layer 112, as shown in FIG. 16, to accommodate a gradually narrowing lumen. Those skilled in the art should understand that, in some embodiments, the radial dimension of the proximal end of the outer layer 112 may be equal to or smaller than the radial dimension of the distal end of the outer layer 112. The inner layer 111 can be turned outward at the turnable region 114 to form the outer layer 112, or the outer layer 112 can be turned inward at the turnable region 114 to form the inner layer 111. Through the turning between the inner layer 111 and the outer layer 112, the growable tube 110 can be grown toward a distal end (e.g., extended or stretched) or withdrawn, so that the growable continuum instrument 500 can grow to reach a target position in the lumen 115 or withdraw from lumen 115. For example, the inner layer 111 is moved to the distal end by a length L, and the inner layer 111 with length L is turned outward in the turnable region 114 to form the outer layer 112, and the fluid 140 fills the fluid chamber 113 grown by the outward turning of the inner layer 111, thereby, the growable tube 110 can grow forward. The inner layer 111 is moved to the proximal end by a length L' and the outer layer 112 with length L' is turned inward in the turnable region 114 to form the inner layer 111, so that the growable tube 110 can withdraw.

As shown in FIG. 16, the inner layer 111 of the growable tube 110 surrounds and forms a channel 1111, the continuum instrument 100 (or continuum instrument 200, 300) of the growable continuum instrument 500 is disposed in the channel 1111, and one or more serially connected continuum structures (e.g., the continuum structures 1000, 2000, 3000, 4000) of the continuum instrument 100 (or the continuum instrument 200, 300) can drive the growable tube 110 to bend when bending. Through the bending guide from one or more continuum structures, the turning of the growable tube 110 can be realized to accommodate the curved and complex lumen 115. Thus, the growable tube 110 can grow distally, through the lumen 115, and grow to a target location. In some embodiments, the radial dimension of the proximal end of outer layer 112 may be larger than the radial dimension of the distal end of outer layer 112. In this manner, the growable instrument 100 is able to accommodate the gradually narrowing lumen 115 to reduce or avoid touching and rubbing against the lumen 115.

Figure 18A:
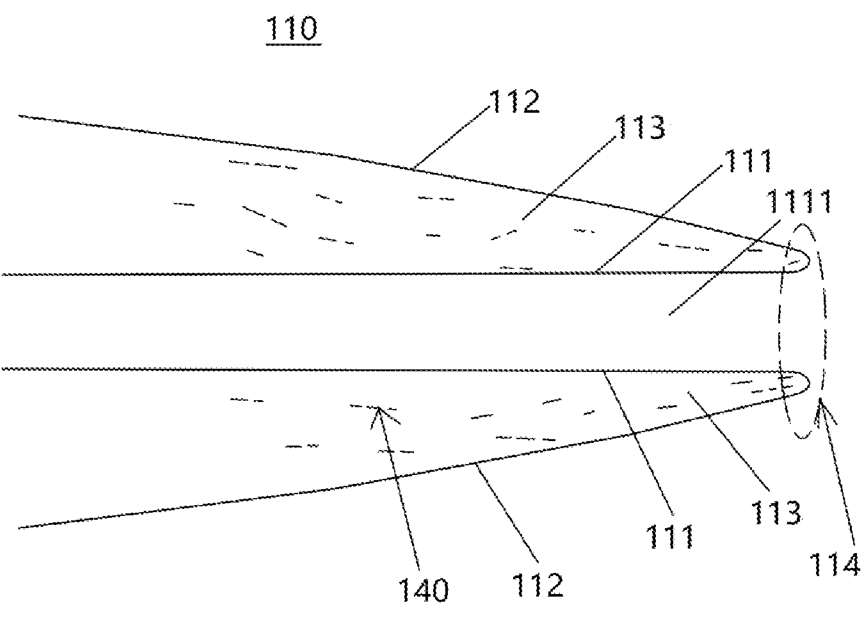
FIG. 18(*a*) shows a structural schematic diagram of a distal portion of a growable tube according to some embodiments of the present disclosure.
Figure 18B:
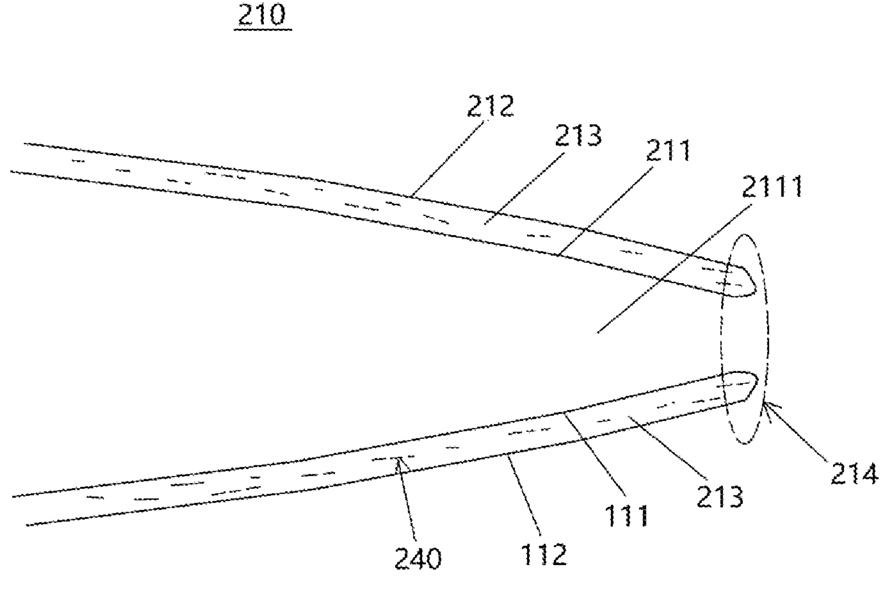

FIG. 18(*a*) and FIG. 18(*b*) respectively show the structural schematic diagrams of the distal portions of the progressive growable tubes 110 and 210 according to some embodiments of the present disclosure. It can be understood that the shape and status of the growable tubes 110 and 210 shown in FIG. 18(*a*) and FIG. 18(*b*) can be the shape and status during the growth process or the shape and status when the growth stops.

As shown in FIG. 18(*a*), in some embodiments, the radial dimension of the outer layer 112 may gradually decrease from the proximal end to the distal end along the extending direction. The contour of the outer layer 112 may be straight, curved, or a combination thereof. The inner layer 111 of the growable tube 110 can remain substantially constant from the proximal end to the distal end along the extending direction. In a state where the turning stops (such as a fully grown state, or when approaching the lesion), the thickness of the fluid chamber 113 gradually increases from the proximal end to the distal end along the extending direction. The inner layer 111 surrounds and forms a channel 1111. The radial dimension of the channel 1111 remains substantially constant from the proximal end to the distal end along the extending direction. The channel 1111 can be used to accommodate the continuum structure (for example, continuum structures 1000, 2000, 3000, 4000) of the continuum instrument 100 (or 200, 300) Either the inner layer 111 or the outer layer 112 can be driven to move distally or proximally.

As shown in FIG. 18(*b*), the radial dimension of the outer layer 212 may gradually decrease from the proximal end to the distal end along the extending direction. The contour of the outer layer 212 may be straight, curved, or a combination thereof. The inner layer 211 of the growable tube 210 can gradually decrease from the proximal end to the distal end along the extending direction. In a state where the turning stops (such as a fully grown state, or when approaching the lesion), the thickness of the fluid chamber 213 remains substantially constant or gradually decreases from the proximal end to the distal end along the extending direction. The inner layer 211 surrounds and forms a channel 2111, and the radial dimension of the channel 2111 gradually decreases from the proximal end to the distal end along the extending direction. The channel 2111 may be used to accommodate a continuum structure (e.g., continuum structure 1000, 2000, 3000, 4000) of the continuum instrument 100 (or 200, 300). Either the inner layer 111 or the outer layer 112 can be driven to move distally or proximally, such that the inner layer 211 can be turned outward at the turnable region 214 to form the outer layer 212, or the outer layer 212 can be turned inward at the turnable region 214 to form the inner layer 211.

It should be understood that the radial dimension of the outer layer 212 may include, but is not limited to, substantially constant, gradually decreasing, or step-wise decreasing from the proximal end to the distal end along the extending direction; and/or the radial dimension of the inner layer 211 may include, but not limited to, remaining constant or gradually decreasing from the proximal end to the distal end along the extending direction. The radial dimensions of the outer layer 212 and the inner layer 211 can be combined by any one of the above.

Figure 19A:
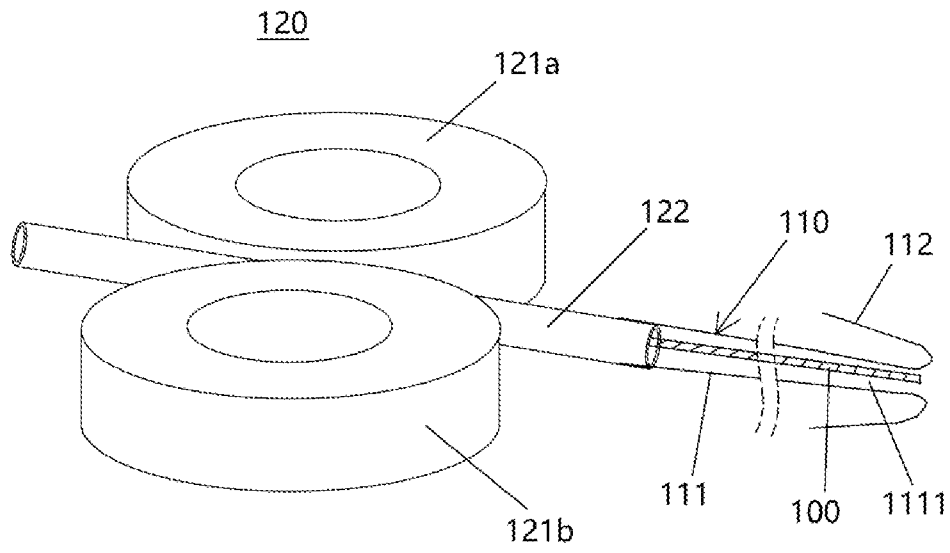
FIG. 19(*a*) shows a structural schematic diagram of a part of a tubular driving mechanism according to some embodiments of the present disclosure.
Figure 19B:
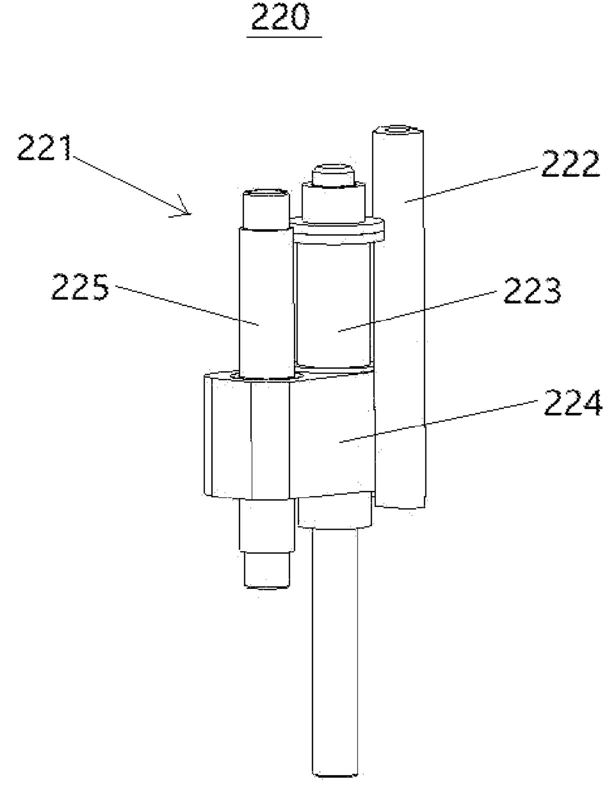

In some embodiments, the growable continuum instrument 500 may also include a tube-driving mechanism 120. FIG. 19(*a*) shows a structural schematic diagram of a part of a tube-driving mechanism according to some embodiments of the present disclosure. As shown in FIG. 19(*a*), the tube-driving mechanism 120 is connected to the growable tube 110 (or 210), and the tube-driving mechanism 120 can move linearly to drive the outer layer 112 or the inner layer 111 of the growable tube 110 to move. In some embodiments, the tube-driving mechanism 120 can be connected to the outer layer 112 of the growable tube 110, thereby driving the outer layer 112 of the growable tube 110 to move. In some embodiments, as shown in FIG. 19(*a*), the tube-driving mechanism 120 may be connected to the inner layer 111 of the growable tube 110 to drive the inner layer 111 of the growable tube 110 to move.

In some embodiments, the tube-driving mechanism 120 may include a driving unit (not shown in the figure), a moving rod 122 and a transmission unit connected with the driving unit and the moving rod 122. The moving rod 122 is sealingly connected with the inner layer or the outer layer of the growable tube 110 (or 210), and the transmission unit is used to convert the rotational motion of the driving unit into a linear motion to drive the moving rod 122 to drive the growable tube 110 (or 210) to grow or withdraw.

In some embodiments, as shown in FIG. 19(*a*), the transmission unit may include two rollers 121*a* and 121*b* arranged side by side. The moving rod 122 is arranged between two rollers 121*a-b*, and the two rollers 121*a-b* are respectively connected to the driving unit. The inner layer 111 of the growable tube 110 (or 210) is sealingly connected to the outer periphery of a distal end of the travel rod 122. The driving unit respectively drives the two rollers 121*a-b* to synchronously rotate in opposite directions at the same speed to drive the moving rod 122 to move linearly, so that the inner layer 111 of the growable tube 110 is driven to move through the moving rod 122. The moving rod 122 drives the inner layer 111 to move distally. In the turnable region 114, the inner layer 111 is turned outward to form the outer layer 112, so that the fluid 140 fills the fluid chamber 113 that grows with the inner layer 111 turning outward. In some embodiments, the distance that the growable tube 110 extends originating from the inner layer 111 turning outward is about the same as the distance for which the moving rod 122 moves. In some embodiments, the distance that the growable tube 110 extends originating from the inner layer 111 turning outward is less than the distance for which that the moving rod 122 moves.

In some embodiments, FIG. 19(*b*) shows a structural schematic diagram of a part of the tube-driving mechanism 220 according to some embodiments of the present disclosure. In some embodiments, as shown in FIG. 19(*b*), the tube-driving mechanism 220 may include a screw slider module 221 and a moving rod 222 driven by the screw slider module 221. The screw slider module 221 may include a screw 223 and a slider 224 connected by threads, and a driving unit (not shown in the figure) connected to the screw 223, and the slider 224 is fixedly connected to the moving rod 222. In some embodiments, the screw slider module 221 may further include a guide rod 225 disposed in the slider 224 by sliding through the slider 224. The outer layer 112 or the inner layer 111 of the growable tube 110 (or 210) is sealingly connected with the moving rod 222. The driving unit drives the screw 223 to rotate, the slider 224 can move linearly along the guide rod 225, and drives the moving rod 222 fixedly connected to the slider 224 to move linearly, thereby driving the outer layer 112 or the inner layer 111 of the growable tube 110 to move.

It should be understood that the tube-driving mechanism of the present disclosure includes but is not limited to the structures of the above embodiments, any driving mechanism, as long as capable of realizing linear motion, does not depart from the scope of the present disclosure.

In some embodiments, the growable continuum instrument 500 may also include a fluid controller (not shown in the figure), which is used to pressurize or depressurize the fluid to drive fluid to fill the fluid chamber 113 of the turnable region or drive fluid to withdrawn from the fluid chamber 113. The fluid controller may include a fluid pump for maintaining the hydraulic pressure in the fluid chamber 113, for example, filling the fluid chamber 113 with fluid during the forward growth of the growable tube 110, or drawing away fluid from the fluid chamber 113 during the withdrawal of the growable tube 110.

Figure 20:
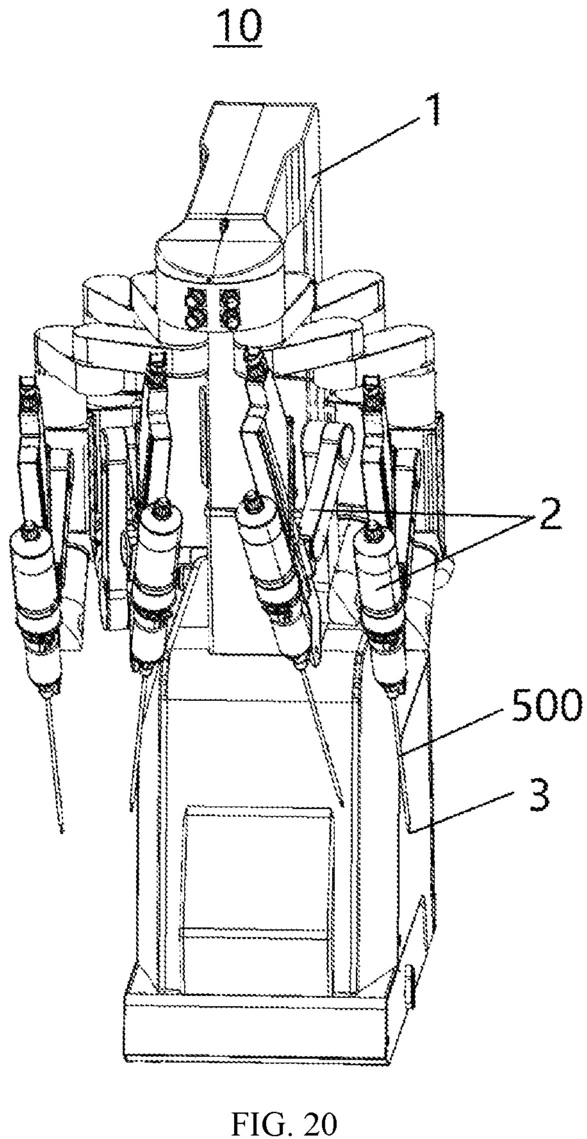
FIG. 20 shows a structural schematic diagram of a surgical robot according to some embodiments of the present disclosure.

In some embodiments, as shown in FIG. 20, the present disclosure also provides a surgical robot 10 that may include the growable continuum instrument 500 in any embodiment disclosed above. In some embodiments, the surgical robot 10 may include a base 1, one or more robotic arms 2, and one or more growable continuum instruments 500 disposed at the ends of the robotic arms 2. The continuum instrument 500 may include a growable tube (for example, the growable tube 110, 210) and a continuum instrument (for example, the continuum instrument 100, 200, 300), and the continuum instrument (for example the continuum instrument 100, 200, 300) includes one or more serially connected continuum structures (for example, continuum structures 1000, 2000, 3000, 4000) and an end tool 3 disposed at the distal end of the continuum structure. The end tool 3 may include, but is not limited to, a surgical actuator, an imaging device, an illumination device, an ultrasonic probe, a probe, or a drug delivery device and the like. The one or more robotic arms 2 have multiple degrees of freedom and can be disposed on the base 1, and one or more growable continuum instruments 500 are detachably disposed on the one or more robotic arms 2, and one or more robotic arms 2 are used to adjust the position and orientation of one or more growable continuum instruments 500. It should be understood that the surgical robot 10 can extend into the lumen through one or more growable continuum instruments 500 for intracavitary interventional diagnosis and treatment. The continuum structure (e.g., the continuum structure 1000, 2000, 3000, 4000) of the continuum instrument (e.g., the continuum instrument 100, 200, 300) can adapt to complex bending environment without causing injury to the lumen through the staggered flexible structural bones (e.g., flexible structural bones 1110, 2110, 3110, 4110).

Note that the above are only exemplary embodiments of the present disclosure and the applied technical principles. Those skilled in the art would appreciate that the present disclosure is not limited to specific embodiments herein, and those skilled in the art could make various apparent changes, readjustments and substitutions without departing from the scope of protection of the present disclosure. Thus, although the present disclosure is described in more detail by the above embodiments, the present disclosure is not limited to the above embodiments. Without departing from the concept of the present disclosure, more other equivalent embodiments may be included, and the scope of the present disclosure is determined by the scope of the appended claims.

The invention claimed is:

1. A growable continuum instrument, comprising:

a growable tube comprising an inner layer, an outer layer, and a fluid chamber between the inner layer and the outer layer, the fluid chamber being used to accommodating fluid; the growable tube comprising a turnable region located at a distal end and at which the inner layer and the outer layer are connected and turnable; and one or more serially connected continuum structures disposed in a channel surrounded by the inner layer of the growable tube, the one or more continuum structures being bendable to drive the growable tube to bend, wherein each continuum structure comprising:

a plurality of spacer discs; and a plurality of connecting structures, wherein the plurality of connecting structures comprise one or more first connecting structures and one or more second connecting structures, wherein each first connecting structure comprises one or more first flexible structural bones, and a first end and a second end of the one or more first flexible structural bones are respectively fixedly connected with first adjacent spacer discs from the plurality of spacer discs, wherein each second connecting structure comprises one or more second flexible structural bones, and a first end and a second end of the one or more second flexible structural bones are respectively fixedly connected with second adjacent spacer discs from the plurality of spacer discs, wherein a distribution of the one or more first flexible structural bones along a circumferential direction of the spacer discs is different from a distribution of the one or more second flexible structural bones along the circumferential direction of the spacer discs, wherein the one or more first connecting structures are serially connected and the one or more second connecting structures are serially connected, wherein the one or more first connecting structures and the one or more second connecting structures alternate periodically or non-periodically along an axial direction of the continuum structure, and wherein each continuum structure further comprises a plurality of driving structural bones that pass through the plurality of spacer discs along the axial direction of the continuum structure, first ends of the plurality of driving structural bones are fixedly connected to a spacer disc located at a farthest end of the plurality of spacer discs, and second ends of the plurality of driving structural bones are used to receive drive to independently drive the continuum structure to bend, wherein for at least one continuum structure from the one or more continuum structures:

the one or more first flexible structural bones and the one or more second flexible structural bones are distributed differently along a first inner contour line on the plurality of spacer discs, and the plurality of driving structural bones are distributed along a second inner contour line that is radially spaced from the first inner contour line on the plurality of spacer discs, wherein projections of an entirety of the first flexible structural bones and the second flexible structural bones along the axial direction of the at least one continuum structure form at least one flexible structural bone high-density distribution area and at least one flexible structural bone low-density distribution area that are distributed along the first inner contour line, the plurality of driving structural bones form at least one driving structural bone high-density distribution area generally opposite to the at least one flexible structural bone high-density distribution area and at least one driving structural bone low-density distribution area generally opposite to the at least one flexible structural bone low-density distribution area that are distributed along the second inner contour line.

2. The growable continuum instrument according to claim 1, wherein a radial dimension of the outer layer is substantially constant, gradually decreases or step-wise decreases from a proximal end to a distal end along an extending direction; or wherein a radial dimension of the inner layer remains constant or gradually decreases from the proximal end to the distal end along the extending direction.

3. The growable continuum instrument according to claim 1, wherein the outer layer is turned inward in the turnable region or the inner layer is turned outward in the turnable region.

4. The growable continuum instrument according to claim 1, wherein the one or more continuum structures comprise a first continuum structure and a second continuum structure connected in series with the first continuum structure, and wherein an easy-to-bend direction of the first continuum structure is different from an easy-to-bend direction of the second continuum structure, or a bending curvature of the first continuum structure is different from a bending curvature of the second continuum structure.

5. The growable continuum instrument according to claim 1, wherein for the at least one continuum structure, the plurality of connecting structures further comprise one or more types of additional connecting structures, the one or more types of additional connecting structures are serially connected, and the one or more first connecting structures and the one or more second connecting structures are distributed periodically or non-periodically along the axial direction of the at least one continuum structure.

6. The growable continuum instrument according to claim 1, wherein the one or more continuum structures comprise a first continuum structure and a second continuum structure connected in series with the first continuum structure, and wherein the second continuum structure and the first continuum structure are structurally the same and are staggered by an included angle along an circumferential direction of the continuum instrument.

7. The growable continuum instrument according to claim 1, wherein for the at least one continuum structure, at least one of the one or more first connecting structures comprises one first flexible structural bone, at least one of the one or more second connecting structures comprises one second flexible structural bone, and the one first flexible structural bone and the one second flexible structural bone are staggered by an included angle along the circumferential direction of the spacer discs.

8. The growable continuum instrument according to claim 1, wherein for the at least one continuum structure, at least one of the one or more first connecting structures comprises a plurality of first flexible structural bones, at least one of the second connecting structures comprises a plurality of second flexible structural bones, wherein the plurality of first flexible structural bones form a first connecting line, and the plurality of second flexible structural bones form a second connecting line, and wherein the first connecting line and the second connecting line comprise at least one of the following distributions: the first connecting line and the second connecting line intersect at an angle at a central axis of the at least one continuum structure, the first connecting line passes through the central axis of the at least one continuum structure and intersects with the second connecting line at an angle outside the central axis of the at least one continuum structure, the first connecting line and the second connecting line deviate from the central axis of the at least one continuum structure and intersect, or the first connecting line and the second connecting line deviate from the central axis of the at least one continuum structure and intersect on their extended lines.

9. The growable continuum instrument according to claim 1, wherein for the at least one continuum structure, at least one of the one or more first connecting structures comprises a plurality of first flexible structural bones, at least one of the one or more second connecting structures comprises a plurality of second flexible structural bones, wherein the plurality of first flexible structural bones form a first curve, and the plurality of second flexible structural bones form a second curve, and wherein the first curve and the second curve comprise at least one of the following distributions: the first curve partially overlaps with the second curve, the first curve is adjacent to the second curve, the first curve is opposite to the second curve, the first curve is circumferentially spaced from the second curve, the first curve is an arc, or the second curve is an arc.

10. The growable continuum instrument according to claim 1, wherein for the at least one continuum structure, wherein projections of the one or more first flexible structural bones and the one or more second flexible structural bones along an axial direction of the at least one continuum structure form a semicircle.

11. The growable continuum instrument according to claim 1, wherein the plurality of driving structural bones comprise driving structural bones distributed in a middle of the driving structural bone high-density distribution or driving structural bones distributed in a middle of the driving structural bone low-density distribution area.

12. The growable continuum instrument according to claim 1, wherein the plurality of spacer discs comprise one or more first mounting holes distributed along a first inner contour line and one or more second mounting holes distributed along a second inner contour line, wherein the one or more first flexible structural bones are fixedly connected to corresponding first mounting holes of the first adjacent spacer discs, and the one or more second flexible structural bones are fixedly connected to corresponding first mounting holes of the second adjacent spacer discs, and wherein the plurality of driving structural bones are disposed in corresponding second mounting holes of the plurality of spacer discs by sliding through therein.

13. The growable continuum instrument according to claim 12, wherein the first inner contour line is at a first distance away from a central axis of the at least one continuum structure, wherein the second inner contour line is at a second distance from the central axis of the at least one continuum structure, and wherein the second distance is greater than the first distance.

14. The growable continuum instrument according to claim 1, further comprising:

a tube-driving mechanism connected to the growable tube, for driving the outer layer or the inner layer of the growable tube to move, wherein the tube-driving mechanism comprises a driving unit, a moving rod, and a transmission unit connected with the driving unit and the moving rod, and wherein the moving rod is sealingly connected with the inner layer or the outer layer of the growable tube, and the transmission unit is used to convert rotary motion of the driving unit into linear motion, so as to drive the moving rod to drive the growable tube to grow or withdraw.

15. The growable continuum instrument according to claim 14, further comprising:

a fluid controller for pressurizing or depressurizing the fluid, to drive the fluid to fill the fluid chamber of the turnable region or drive the fluid to withdraw from the fluid chamber.

16. A surgical robot, comprising:

a growable continuum instrument, comprising:

a growable tube comprising an inner layer, an outer layer, and a fluid chamber between the inner layer and the outer layer, the fluid chamber being used to accommodating fluid; the growable tube comprising a turnable region located at a distal end and at which the inner layer and the outer layer are connected and turnable; and one or more serially connected continuum structures disposed in a channel surrounded by the inner layer of the growable tube, the one or more continuum structures being bendable to drive the growable tube to bend, wherein each continuum structure comprising:

a plurality of spacer discs; and a plurality of connecting structures, wherein the plurality of connecting structures comprise one or more first connecting structures and one or more second connecting structures, wherein each first connecting structure comprises one or more first flexible structural bones, and a first end and a second end of the one or more first flexible structural bones are respectively fixedly connected with first adjacent spacer discs from the plurality of spacer discs, wherein each second connecting structure comprises one or more second flexible structural bones, and a first end and a second end of the one or more second flexible structural bones are respectively fixedly connected with second adjacent spacer discs from the plurality of spacer discs, wherein a distribution of the one or more first flexible structural bones along a circumferential direction of the spacer discs is different from a distribution of the one or more second flexible structural bones along the circumferential direction of the spacer discs, wherein the one or more first connecting structures are serially connected and the one or more second connecting structures are serially connected, wherein the one or more first connecting structures and the one or more second connecting structures alternate periodically or non-periodically along an axial direction of the continuum structure, and wherein each continuum structure further comprises a plurality of driving structural bones that pass through the plurality of spacer discs along the axial direction of the continuum structure, first ends of the plurality of driving structural bones are fixedly connected to a spacer disc located at a farthest end of the plurality of spacer discs, and second ends of the plurality of driving structural bones are used to receive drive to independently drive the continuum structure to bend, wherein for at least one continuum structure from the one or more continuum structures:

the one or more first flexible structural bones and the one or more second flexible structural bones are distributed differently along a first inner contour line on the plurality of spacer discs, and the plurality of driving structural bones are distributed along a second inner contour line that is radially spaced from the first inner contour line on the plurality of spacer discs, wherein projections of an entirety of the first flexible structural bones and the second flexible structural bones along the axial direction of the at least one continuum structure form at least one flexible structural bone high-density distribution area and at least one flexible structural bone low-density distribution area that are distributed along the first inner contour line, the plurality of driving structural bones form at least one driving structural bone high-density distribution area generally opposite to the at least one flexible structural bone high-density distribution area and at least one driving structural bone low-density distribution area generally opposite to the at least one flexible structural bone low-density distribution area that are distributed along the second inner contour line.

* * * * *